US008563528B2

(12) United States Patent
Straarup et al.

(10) Patent No.: US 8,563,528 B2
(45) Date of Patent: Oct. 22, 2013

(54) ANTISENSE OLIGOMERS TARGETING PCSK9

(75) Inventors: Ellen Marie Straarup, Birkerød (DK); Niels Fisker Nielsen, Lyngby (DK); Marie Lindholm, Malmö (SE); Joacim Elmèn, Malmö (SE)

(73) Assignee: Santaris Pharma A/S, Horsholm (DK)

( * ) Notice: Subject to any disclaimer, the term of this patent is extended or adjusted under 35 U.S.C. 154(b) by 122 days.

(21) Appl. No.: 13/139,696

(22) PCT Filed: Jun. 30, 2010

(86) PCT No.: PCT/EP2010/059257
§ 371 (c)(1),
(2), (4) Date: Oct. 11, 2011

(87) PCT Pub. No.: WO2011/009697
PCT Pub. Date: Jan. 27, 2011

(65) Prior Publication Data
US 2012/0122954 A1 May 17, 2012

Related U.S. Application Data

(60) Provisional application No. 61/227,109, filed on Jul. 21, 2009, provisional application No. 61/253,090, filed on Oct. 20, 2009, provisional application No. 61/311,788, filed on Mar. 9, 2010, provisional application No. 61/321,892, filed on Apr. 8, 2010.

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC .................................. 514/44 A; 536/24.5

(58) Field of Classification Search
USPC ............................. 536/24.1, 24.5
See application file for complete search history.

(56) References Cited

U.S. PATENT DOCUMENTS

| 4,914,210 A | 4/1990 | Levenson et al. |
| 4,962,029 A | 10/1990 | Levenson et al. |
| 5,919,795 A | 7/1999 | Chang et al. |
| 6,030,785 A | 2/2000 | Katze et al. |

(Continued)

FOREIGN PATENT DOCUMENTS

| EP | 0 699 751 A1 | 3/1996 |
| EP | 1 099 442 A2 | 5/2001 |

(Continued)

OTHER PUBLICATIONS

Beaucage, S.L. and Iyer, R.P., "Advances in the Synthesis of Oligonucleotides by the Phosphoramidite Approach," *Tetrahedron* 48(12):2223-2311, Pergamon Press Ltd., United Kingdom (1992).

(Continued)

*Primary Examiner* — Terra Cotta Gibbs
(74) *Attorney, Agent, or Firm* — Sterne, Kessler, Goldstein & Fox P.L.L.C.

(57) ABSTRACT

The present invention relates to oligomer compounds (oligomers), which target PCSK9 mRNA in a cell, leading to reduced expression of PCSK9. Reduction of PCSK9 expression is beneficial for the treatment of certain medical disorders, such as hypercholesterolemia and related disorders.

22 Claims, 8 Drawing Sheets

(56) References Cited

U.S. PATENT DOCUMENTS

| | | | |
|---|---|---|---|
| 6,121,283 | A | 9/2000 | Chang et al. |
| 6,284,458 | B1 | 9/2001 | Anderson et al. |
| 6,423,489 | B1 | 7/2002 | Anderson et al. |
| 6,433,159 | B1 | 8/2002 | Anderson |
| 7,029,895 | B2 | 4/2006 | Glucksmann et al. |
| 7,087,229 | B2 | 8/2006 | Zhao et al. |
| 7,605,251 | B2 | 10/2009 | Tan et al. |
| 7,683,036 | B2 | 3/2010 | Esau et al. |
| 7,687,617 | B2 | 3/2010 | Thrue et al. |
| 7,737,264 | B2 | 6/2010 | Thrue et al. |
| 7,888,324 | B2 | 2/2011 | Crooke et al. |
| 8,143,230 | B2 | 3/2012 | Bhanot et al. |
| 2003/0125241 | A1 | 7/2003 | Wissenbach et al. |
| 2003/0199467 | A1 | 10/2003 | Roberts et al. |
| 2005/0069522 | A1 | 3/2005 | Colonno et al. |
| 2006/0035212 | A1 | 2/2006 | Balakireva |
| 2006/0035858 | A1 | 2/2006 | Geary et al. |
| 2006/0040989 | A1 | 2/2006 | Meerpoel et al. |
| 2006/0185027 | A1 | 8/2006 | Bartel et al. |
| 2007/0173473 | A1* | 7/2007 | McSwiggen et al. ........... 514/44 |
| 2008/0015162 | A1 | 1/2008 | Bhanot et al. |
| 2009/0318536 | A1 | 12/2009 | Freier et al. |
| 2010/0144834 | A1 | 6/2010 | Freier et al. |
| 2010/0216864 | A1 | 8/2010 | Straarup et al. |
| 2011/0224280 | A1 | 9/2011 | Nielsen et al. |

FOREIGN PATENT DOCUMENTS

| | | |
|---|---|---|
| EP | 0 662 157 B1 | 6/2001 |
| EP | 1 222 309 B1 | 7/2005 |
| WO | WO 95/30746 A1 | 11/1995 |
| WO | WO 99/14226 A2 | 3/1999 |
| WO | WO 00/56746 A2 | 9/2000 |
| WO | WO 00/56748 A1 | 9/2000 |
| WO | WO 00/66604 A2 | 11/2000 |
| WO | WO 01/23613 A1 | 4/2001 |
| WO | WO 01/25248 A2 | 4/2001 |
| WO | WO 01/48190 A2 | 7/2001 |
| WO | WO 01/57081 A2 | 8/2001 |
| WO | WO 02/28875 A2 | 4/2002 |
| WO | WO 02/094250 A2 | 11/2002 |
| WO | WO 03/006475 A2 | 1/2003 |
| WO | WO 03/011887 A2 | 2/2003 |
| WO | WO 03/085110 A2 | 10/2003 |
| WO | WO 03/095467 A1 | 11/2003 |
| WO | WO 2004/044181 A2 | 5/2004 |
| WO | WO 2004/046160 A2 | 6/2004 |
| WO | WO 2004/069991 A2 | 8/2004 |
| WO | WO 2004/097047 A1 | 11/2004 |
| WO | WO 2005/013901 A2 | 2/2005 |
| WO | WO 2005/023825 A2 | 3/2005 |
| WO | WO 2005/054494 A2 | 6/2005 |
| WO | WO 2005/058824 A2 | 6/2005 |
| WO | WO 2005/061710 A1 | 7/2005 |
| WO | WO 2005/073378 A1 | 8/2005 |
| WO | WO 2005/098029 A2 | 10/2005 |
| WO | WO 2005/107816 A2 | 11/2005 |
| WO | WO 2006/010423 A2 | 2/2006 |
| WO | WO 2006/020676 A2 | 2/2006 |
| WO | WO 2006/020768 A2 | 2/2006 |
| WO | WO 2006/036916 A2 | 4/2006 |
| WO | WO 2006/053430 A1 | 5/2006 |
| WO | WO 2006/093526 A2 | 9/2006 |
| WO | WO 2006/112872 A2 | 10/2006 |
| WO | WO 2006/113910 A2 | 10/2006 |
| WO | WO 2007/031081 A2 | 3/2007 |
| WO | WO 2007/031091 A2 | 3/2007 |
| WO | WO 2007/690071 A2 | 8/2007 |
| WO | WO 2007/112753 A2 | 10/2007 |
| WO | WO 2007/112754 A2 | 10/2007 |
| WO | WO 2007/131237 A2 | 11/2007 |
| WO | WO 2007/134181 A2 | 11/2007 |
| WO | WO 2007/143315 A2 | 12/2007 |
| WO | WO 2007/146511 A1 | 12/2007 |
| WO | WO 2008/011431 A2 | 1/2008 |
| WO | WO 2008/034122 A2 | 3/2008 |
| WO | WO 2008/034123 A2 | 3/2008 |
| WO | WO 2008/043753 A2 | 4/2008 |
| WO | WO 2008/061537 A2 | 5/2008 |
| WO | WO 2008/066776 A2 | 6/2008 |
| WO | WO 2008/089767 A1 | 7/2008 |
| WO | WO 2008/109472 A2 | 9/2008 |
| WO | WO 2008/124384 A2 | 10/2008 |
| WO | WO 2008/150729 A2 | 12/2008 |
| WO | WO 2008/154401 A2 | 12/2008 |
| WO | WO 2009/020771 A2 | 2/2009 |
| WO | WO 2009/067647 A1 | 5/2009 |
| WO | WO 2009/090182 A1 | 7/2009 |
| WO | WO 2009/127680 A1 | 10/2009 |
| WO | WO 2009/148605 A2 | 12/2009 |
| WO | WO 2011/009697 A1 | 1/2011 |

OTHER PUBLICATIONS

Beaucage, S.L. and Iyer, R.P., "The Synthesis of Modified Oligonucleotides by the Phosphoramidite Approach and Their Applications," *Tetrahedron* 49(28):6123-6194, Pergamon Press Ltd., United Kingdom (1993).

Braasch, D.A., et al., "Antisense inhibition of gene expresson in cells by oligonucleotides incorporating locked nucleic acids: effect of mRNA target sequence and chimera design," *Nucleic Acids Res.* 30(23):5160-5167, Oxford University Press, United Kingdom (2002).

Christensen, U.B. and Pedersen, E.B., "Intercalating nucleic acids containing insertions of 1-O-(1-pyrenylmethyl)glycerol: stabilisation of dsDNA and discrimination of DNA over RNA," *Nucleic Acids Res.* 30(22):4918-4925, Oxford University Press, United Kingdom (2002).

Costet, P., et al., "Hepatic PCSK9 Expression Is Regulated by Nutritional Status via Insulin and Sterol Regulatory Element-binding Protein 1c," *J. Biol. Chem.* 281(10):6211-6218, The American Society for Biochemistry and Molecular Biology, Inc., United States (2006).

Crooke, R.M., "Chapter 3: In Vitro Cellular Uptake, Distribution, and Metabolism of Oligonucleotides," in *Antisense Research and Application*, pp. 103-140, Cooke, S.T., ed., Springer-Verlag, Germany (1998).

Dass, C.R., "Vehicles for oligonucleotide delivery to tumours," *J. Pharm. Pharmacol.* 54:3-27, Pharmaceutical Press, United Kingdom (2002).

Davidson, N.O. and Shelness, G.S., "Apolipoprotein B: mRNA Editing, Lipoprotein Assembly, and Presecretory Degradation," *Annu. Rev. Nutr.* 20:169-193, Annual Reviews, United States (2000).

Davis, S., et al., "Improved targeting of miRNA with antisense oligonucleotides," *Nucleic Acids Res.* 34(8):2294-2304, Oxford University Press, United Kingdom (2006).

Deere, J., et al., "Antisense Phosphorodiamidate Morpholino Oligomer Length and Target Position Effects on Gene-Specific Inhibition in *Eschericia coli*," *Antimicrobal Agents and Chemotherapy* 49(1):249-255, American Society for Microbiology, United States (2005).

Elbashir, S.M., et al., "Analysis of gene function in somatic mammalian cells using small interfering RNAs," *Methods* 26:199-213, Elsevier Science, United States (2002).

Elmén, J.J., et al., "Locked nucleic acid containing antisense oligonucleotides enhance inhibition of HIV-1 genome dimerization and inhibit virus replication," *FEBS Letters* 578:285-290, Elsevier B.V., The Netherlands (2004).

Feld, J., et al., "Ribavirin Improves Early Response to Peginterferon Through Improved Interferon Signaling," *Gastroenterology* 139:154-162, AGA Institute, United States (2010).

Freier, S.M. and Altmann, K-H., "The ups and downs of nucleic acid duplex stability: structure—stability studies on chemically-modified DNA: RNA duplexes," *Nucleic Acids Res.* 25:4429-4443, Oxford University Press, United Kingdom (1997).

Frieden, M., et al., "Expanding the design horizon of antisense oligonucleotides with alpha-L-LNA," *Nucleic Acids Res.* 31(21):6365-6372, Oxford University Press, United Kingdom (2003).

(56) References Cited

OTHER PUBLICATIONS

Gentleman, R.C., et al., "Bioconductor: open software development for computational biology and bioinformatics," *Genome Biol.* 5:R80, BioMed Central Ltd., United Kingdom (2004).
Giles, R.V., et al., "Selecting optimal oligonucleotides composition for maximal antisense effect following streptolysin O-mediated delivery into human leukaemia cells," *Nucleic Acid Res.* 26(7):1567-1575, Oxford University Press, United Kingdom (1998).
Graham, M.J., et al., "Antisense inhibition of proprotein convertase subtilisin/kexin type 9 reduces serum LDL in hyperlipidemic mice," *J. Lipid Res.* 48:763-767, American Society for Biochemistry and Molecular Biology, Inc., United States (2007).
Greene, T. and Wuts, P., *Protective Groups in Organic Synthesis*, [Table of Contents], 3rd ed., John Wiley & Sons, Chichester, England (1999).
Hanecak, R., et al., "Antisense Oligonucleotide Inhibition of Hepatitis C Virus Gene Expression in Transformed Hepatocytes," *J. Virol.* 70(8):5203-5212, American Society For Microbiology, United States (1996).
Heid, C.A., et al., "Real Time Quantitative PCR," *Genome Res.* 6:986-994, Cold Spring Harbor Laboratory Press, United States (1996).
Hu, Q., "Subcellular trafficking of antisesnse oligonucleotides and down-regulation of *bcl*-2 gene expression in human melanoma cells using a fusogenic liposome delivery system," *Nucleic Acids Res.* 30:3632-3641, Oxford University Press, United Kingdom (2002).
Huang, H., et al., "Hepatitis C virus production by human hepatocytes dependent on assembly and secretion of very low-density lipoproteins," *Proc. Natl. Acad, Sci. U.S.A.* 104(14):5848-5853, National Academy of Sciences, United States (2007).
Huber, W., et al., "Variance stabilization applied to microarray data calibration and to the quantification of differential expression," *Bioinformatics 18*:S96-S104, Oxford University Press, United Kingdom (2002).
Hutton, J.R., "Renaturation kinetics and thermal stability of DNA in aqueous solutions of formamide and urea," *Nucleic Acids Res.* 4(10):3537-3555, Information Retrieval Limited, United Kingdom (1977).
Hutvágner, G., et al., "A Cellular Function for the RNA-Interference Enzyme Dicer in the Maturation of the *let-7* Small Temporal RNA," *Science 293*:834-838, American Association for the Advancement of Science, United States (2001).
Hutvágner, G., et al., "Sequence-Specific Inihibition of Small RNA Function," *PLoS Biology 2*(4):0465-0475, Public Library of Science, United States (2004).
Ittig, D., et al., "Nuclear antisense effects in cyclophilin A pre-mRNA splicing by oligonucleotides: a comparison of tricyclo-DNA with LNA," *Nucleic Acids Res.* 32(1):346-353, Oxford University Press, United Kingdom (2004).
Jepsen, J.S., et al., "Locked Nucleic Acid: A Potent Nucleic Acid Analog in Therapeutics and Biotechnology," *Oligonucleotides 14*:130-146, Mary Ann Liebert, Inc., United States (2004).
Johansson, H.E., et al., "Target-specific arrest of mRNA translation by antisense 2'-O-alkyloligonucleotides," *Nucleic Acids Res.* 22(22):4591-4598, Oxford University Press, United Kingdom (1994).
Johnson, S.M., et al., "*RAS* is Regulated by the *let-7* MicroRNA Family," *Cell 120*:635-647, Elsevier Inc., United States (2005).
Kauppinen, S., et al., "Locked nucleic acid (LNA): High affinity targeting of RNA for diagnostics and therapeutics," *Drug Discovery Today: Technologies 2*(3):287-290, Elsevier Ltd., Netherlands (2005).
Ketting, R.F., et al., "Dicer functions in RNA interference and in synthesis of small RNA involved in developmental timing in *C.elegans*," *Genes Dev.* 15:2654-2659, Cold Spring Harbor Laboratory Press, United States (2001).
Kloosterman, W.P., et al., "Substrate requirements for *let-7* function in the developing zebrafish embryo," *Nucleic Acids Res.* 32(21):6284-6291, Oxford University Press, United Kingdom (2004).

Krukemeyer, M.G., et al., "Description of B Lymphocytes and Plasma Cells, Complement, and Chemokines/Receptors in Acute Liver Allograft Rejection," *Transplantation 78*(1):65-70, Lippincott Williams & Wilkins, United States (2004).
Krützfeldt, J., et al., "Specificity, duplex degradation and subcellular localization of antagomirs," *Nucleic Acids Res.* 35(9):2885-2892, Oxford University Press, United Kingdom (2007).
Kurreck, J., et al., "Design of antisense oligonucleotides stabilized by locked nucleic acids," *Nucleic Acids Res.* 30(9):1911-1918, Oxford University Press, United Kingdom (2002).
Lalanne, F., et al., "Wild-type PCSK9 inhibits LDL clearance but does not affect apoB-containing lipoprotein production in mouse and cultured cells," *J. Lipid Res.* 46:1312-1319, American Society for Biochemistry and Molecular Biology, United States (2005).
Lambert, G., et al., "*PCSK9*: a promising therapeutic target for dyslipidemias!" *Trends Endocrinol. Metab. 17*:79-81, Elsevier Ltd., Netherlands (2006).
Lanford, R.E., et al., "Antiviral Effect and Virus-Host Interactions in Response to Alpha Interferon, Gamma Interferon, Poly(I)-poly(C), Tumor Necrosis Factor Alpha, and Ribavirin in Hepatitis C Virus Subgenomic Replicons," *J. Virol.* 77(2):1092-1104, American Society for Microbiology, United States (2003).
Lanford, R.E., et al., "Lack of Response to Exogenous Interferon-α in the Liver of Chimpanzees Chronically Infected with Hepatitis C Virus," *Hepatology 46*:999-1008, Wiley Interscience, United States (2007).
Lima, W.F., et al., "Combinatorial Screening and Rational Optimization for Hybridization to Folded Hepatiis C Virus RNA of Oligonucleotides with Biological Antisense Activity," *J. Biol. Chem.* 272(1):626-638, American Society for Biochemical & Molecular Biology, Inc., United States (1997).
Lisziewicz, J., et al., "Long-term treatment of human immunodeficiency virus-infected cells with antisense oligonucleotide phosphorothioates," *Proc. Natl. Acad. Sci. 90*:3860-3864, National Academy of Sciences, United States (1993).
Manoharan, M., et al., "Novel Functionalization of the Sugar Moiety of Nucleic Acids for Multiple Labeling in the Minor Groove," *Tetrahedron Letters 32*(49):7171-7174, Pergamon Press, PLC, United Kingdom (1991).
Martinez, J., et al., "Single-Stranded Antisense siRNAs Guide Target RNA Cleavage in RNAi," *Cell 110*:563-574, Cell Press, United States (2002).
Matz, M., et al., "Early post-transplant urinary IP-10 expression after kidney transplantation is predictive of short- and long-term graft function," *Kidney Int.* 69:1683-1690, International Society of Nephrology, United States (2006).
McManus, M.T., and Sharp, P.A., "Gene Silencing in Mammals by Small Interfering RNAs," *Nat. Rev. 3*:737-747, Nature Publishing Group, United Kingdom (2002).
Möröy, T., et al., "Structure and expression of *hcr*, a locus rearranged with *c-myc* in a woodchuck hepatocellular carcinoma," *Oncogene 4*:59-65, Nature Publishing Group, United Kingdom (1989).
Neuman, B.W., et al., "Antisense Morpholino-Oligomers Directed against the 5' End of the Genome Inhibit Coronavirus Proliferation and Growth," *J. Virol.* 78(11):5891-5899, American Society for Microbiology, United States (2004).
Nulf, C.J. and Corey, D., "Intracellular inhibition of hepatitis C virus (HCV) internal ribosomal entry site (RES)-dependent translation by peptide nucleic acids (PNAs) and locked nucleic acids (LNAs)," *Nucleic Acids Res.* 32(13):3792-3798, Oxford University Press, United Kingdom (2004).
Ørom, U.A., et al., "LNA-modified oligonucleotides mediate specific inhibition of microRNA function," *Gene 372*:137-141, Elsevier B.V., Netherlands (2006).
Park, S.W., et al., "Post-transcriptional Regulation of Low Density Lipoprotein Receptor Protein by Proprotein Convertase Subtilisin/Kexin Type 9a in Mouse Liver," *J. Biol. Chem.* 279(48):50630-50638, American Society for Biochemistry and Molecular Biology, Inc., United States (2004).
Paushkin, S., et al., "The SMN complex, an assemblyosome of ribonucleoproteins," *Curr. Opin. Cell Biol. 14*:305-312, Elsevier Science Ltd., United Kingdom (2002).

(56) References Cited

OTHER PUBLICATIONS

Pedersen, D.S., et al., "Preparation of LNA Phosphoramidites," *Synthesis* 6:802-808, George Thieme Verlag, Germany (2002).

Pedersen, D.S., and Koch, T., "Analogues of LNA (Locked Nucleic Acid). Synthesis of the 2'-Thio-LNA Thymine and 5-Methylcytidine Phosphoramidites," *Synthesis* 4:578-582, George Thieme Verlag, Germany (2003).

Petri, A., et al., "MicroRNA Silencing in Primates: Towards Development of Novel Therapeutics," *Cancer Res.* 69(2):393-395, American Association for Cancer Research, United States (2009).

Prakash, T.P., et al., "Antisense Oligonucleotides Containing Conformationally Constrained 2',4'-(N-Methoxy)aminomethylene and 2',4'-Aminooxymethylene and 2'-O,4'-C-Aminomethylene Bridged Nucleoside Analogues Show Improved Potency in Animal Models," *J. Med. Chem.* 53:1636-1650, American Chemical Society, United States (2010).

Randall, G., et al., "Cellular cofactors affecting hepatitis C virus infection and replication," *Proc. Natl. Acad. Sci. USA* 104(31):12884-12889, National Academy of Sciences, United States (2007).

Rashid, S., et al., "Decreased plasma cholesterol and hypersensitivity to statins in mice lacking Pcsk9," *Proc. Natl. Acad. Sci. U.S.A.* 102(15):5374-5379, National Academy of Sciences, United States (2005).

Rosenbohm, C., et al., "Synthesis of 2'-amino-LNA: a new strategy," *Org. Biomol. Chem.* 1:655-663, Royal Society of Chemistry, United Kingdom (2003).

Saeed, A.I., et al., "TM4: A Free, Open-Source System for Microarray Data Management and Analysis," *BioTechniques* 34:374-378, Informa Healthcare USA, Inc., United Kingdom (2003).

Samuel, D., "Hepatitis C, Interferon, and Risk of Rejection After Liver Transplantation," *Liver Transpl.* 10(7):868-871, Wiley InterScience, United States (2004).

Santaris Pharma, Nature Genetics Ad, "LNA-antimiRs—Toward Effective MicroRNA Antagonist," Jun. 2006 [powerpoint slide], 1 page.

Sazani, P., et al., "Nuclear antisense effects of neutral, anionic and cationic oligonucleotide analogs," *Nucleic Acids. Res.* 29(19):3965-3974, Oxford University Press, United Kingdom (2001).

Schwarz, D.S., et al., "Evidence that siRNAs Function as Guides, Not Primers, in the Drosophila and Human RNAi Pathways," *Mol. Cell* 10:537-548, Cell Press, United States (2002).

Seth, P.P., et al., "Synthesis and Biophysical Evaluation of 2',4'-Constrained 2'O-Methoxyethyl and 2',4'-Constained 2'O-Ethyl Nucleic Acid Analogues," *J. Org. Chem.* 75 1569-1581, American Chemical Society, United States (2010).

Singh, S.K., et al., "Synthesis of Novel Bicyclo[2.2.1] Ribonucleosides: 2'-Amino-and 2'-Thio-LNA Monomeric Nucleosides," *J. Org. Chem.* 63:6078-6079, American Chemical Society, United States (1998).

Sørensen, M.D., et al., "α-L-ribo-Configured Locked Nucleic Acid (α-L-LNA): Synthesis and Properties," *J. Am. Chem. Soc.* 124(10):2164-2176, American Chemical Society, United States (2002).

Tallet-Lopez, B., et al., "Antisense oligonucleotides targeted to the domain IIId of the hepatitis C virus IRES compete with 40S ribosomal subunit binding and prevent in vitro tanslation," *Nucleic Acids Res.* 31(2):734-742, Oxford University Press, United Kingdom (2003).

Tam, W., "Identification and characterization of human BIC, a gene on chromosome 21 that encodes a noncoding RNA," *Gene* 274:157-167, Elsevier Science B.V., Netherlands (2001).

Tijsterman, M., et al., "RNA Helicase MUT-14-Depedent Gene Silencing Triggered in *C. elegans* by Short Antisense RNAs," *Science* 295:694-697, American Association for the Advancement of Science, United States (2002).

Uhlmann, E., "Recent advances in the medicinal chemistry of antisense oligonucleotides," *Curr. Opin. Drug Discov. Develop.* 3:203-213, Pharma Press Ltd., United Kingdom (2000).

Wagner, R.W., "Gene inhibition using antisense oligodeoxynucleotides," *Nature* 372(24):333-335, Nature Publishing Group, United Kingdom (1994).

Wagner, R.W., et al., "Potent and selective inhibition of gene expression by an antisense heptanucleotide," *Nat. Biotechnol.* 14:840-844, Nature Publishing Group, United Kingdom (1996).

Wahlestedt, C., et al., "Potent and nontoxic antisense oligonucleotides containing locked nucleic acids," *Proc. Natl. Acad. Sci. USA* 97(10):5633-5638, National Academy of the Sciences, United States (2000).

Walter, T., et al., "Rejection Under Alpha Interferon Therapy in Liver Transplant Recipients," *Am. J. Transplant.* 7:177-184, Blackwell Munksgaard, Denmark (2007).

Yu, J-Y., et al., "RNA interference by expression of short-interfering RNAs and hairpin RNAs in mammalian cells," *Proc. Natl. Acad. Sci.* 99(9):6047-6052, National Academy of Sciences, United States (2002).

Zhang, H., et al., "Antisense Oligonucleotide Inhibition of Hepatisis C Virus (HCV) Gene Expression in Livers of Mice Infected with an HCV-Vaccinia Virus Recombinant," *Antimicrob. Agents and Chemother.* 43(2):347-353, American Society for Microbiology, United States (1999).

Zhao, Y., et al., "Serum response factor regulates a muscle-specific microRNA that targets Hand2 during cardiogenesis," *Nature* 436:214-220, Nature Publishing Group, United Kingdom (2005).

Bennett, C.F., et al., "An ICAM-1 Antisense Oligonucleotide Prevents and Reverses Dextran Sulfate-Induced Colitis in Mice," *Journal of Pharmacology and Experimental Therapeutics* 280(2):988-1000, American Society for Pharmacology and Experimental Therapeutics, United States (1997).

Fluiter, K., "Filling the gap in LNA antisense oligo gapmers: the effects of unlocked nucleic acid (UNA) and 4'-C-hydroxymethyl-DNA modifications on RNase H recruitment and efficacy of an LNA gapmer," *Molecular BioSystems* 5:838-843, Royal Society of Chemistry, United Kingdom (2009).

Frank-Kamenetsky, M., et al., "Therapeutic RNAi targeting PCSK9 acutely lowers plasma cholesterol in rodents and LDL cholesterol in nonhuman primates," *PNAS* 105(33):11915-11920, National Academy of Sciences, United States (2008).

Gupta, N., et al., "A Locked Nucleic Acid Antisense Oligonucleotide (LNA) Silences PCSK9 and Enhances LDLR Expression In Vitro and In Vivo," *PLoS ONE* 5(5):e10682, 9 pages, Public Library of Science, United States (2010).

Lopez, D., "Inhibition of PCSK9 as a Novel Strategy for the Treatment of Hypercholesterolemia," *Drug News Perspect.* 21(6):323-330, Prous Science, S.A.U., Spain (2008).

Seidah, N.G., "PCSK9 as a therapeutic target of dyslipidemia," *Expert Opin. Ther. Targets* 13(1):19-28, Informa UK Ltd., United Kingdom (2009).

Straarup, E.M., et al., "Short locked nucleic acid antisense oligonucleotides potently reduce apolipoprotein B mRNA and serum cholesterol in mice and non-human primates," *Nucleic Acids Research* 38(20):7100-7111, Oxford University Press, United Kingdom (2010).

NCBI Entrez, GenBank Report, Accession No. NM_174936, Chernogubova, E. et al., Entry Date Jul. 2012.

NCBI Entrez, GenBank Report, Accession No. NP_777596.2, Chernogubova, E. et al., Entry Date Jul. 2012.

International Search Report for International Application No. PCT/EP2007/060703, European Patent Office, Netherlands, mailed on Aug. 13, 2008.

International Search Report for International Application No. PCT/EP2010/059257, European Patent Office, Netherlands, mailed on Nov. 5, 2010.

International Search Report for International Application No. PCT/EP2009/054499, European Patent Office, Netherlands, mailed on Sep. 2, 2009.

Xu, Y., et al., "Effective small interfering RNAs and phosphorothioate antisense DNAs have different preferences for target sites in the luciferase mRNAs," *Biochem Biophys Res Commun.* 306(3):712-7, Elsevier Science, USA (2003).

\* cited by examiner

Figure 1
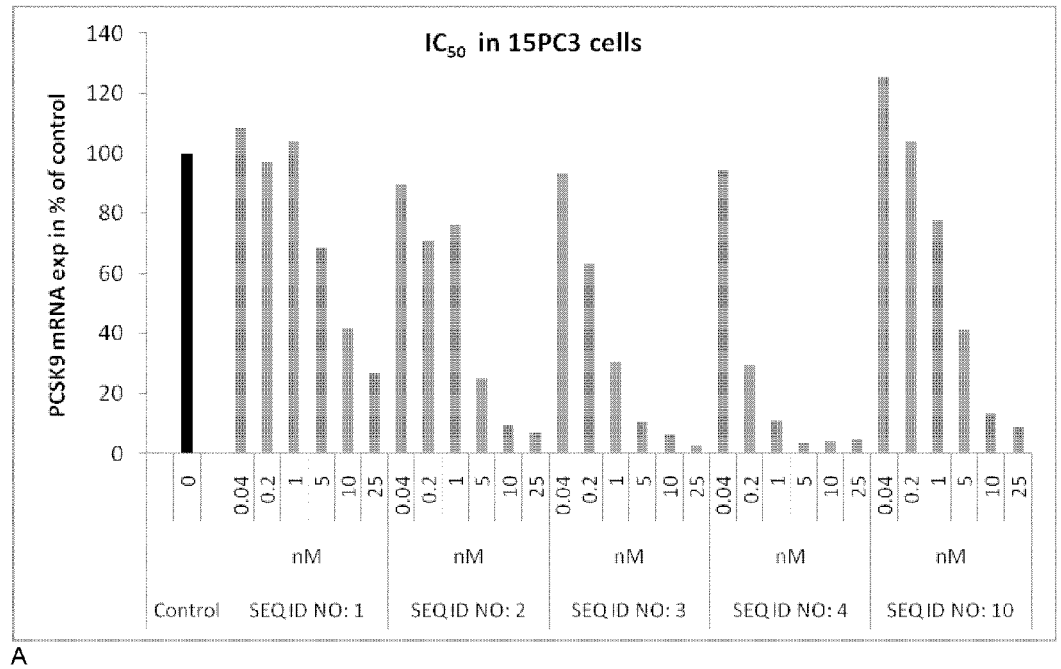
A
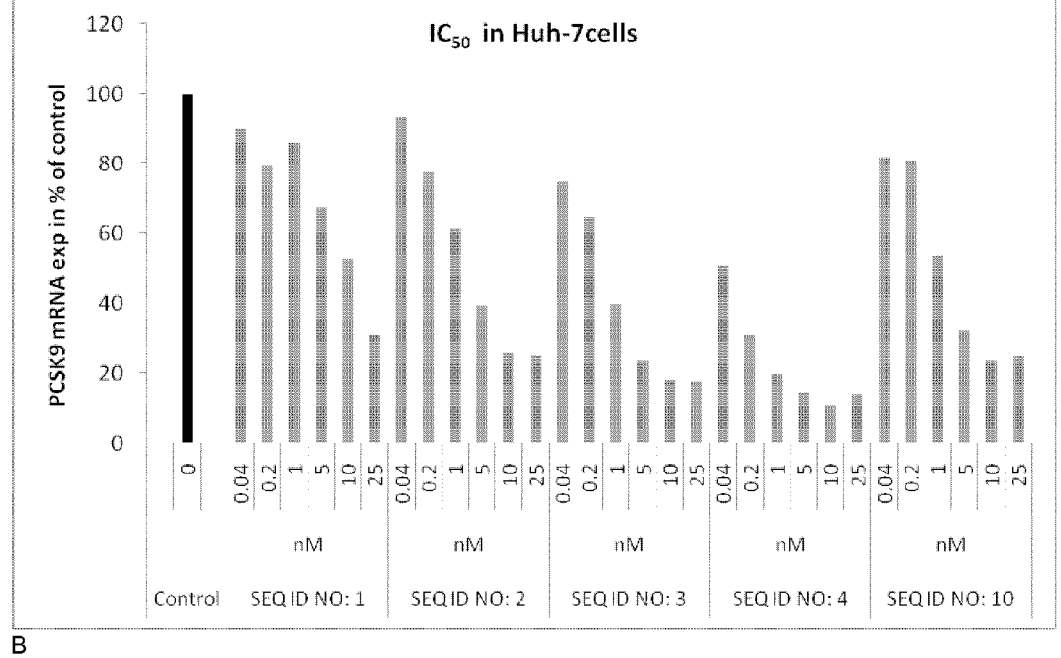
B

Figure 2

|  | SEQ ID NO: 1 | SEQ ID NO: 2 | SEQ ID NO: 3 | SEQ ID NO: 4 | SEQ ID NO: 10 |
|---|---|---|---|---|---|
| IC50 Huh-7 | 7.270 | 0.765 | 0.216 | 0.033 | 0.565 |
| IC50 15PC3 | 5.736 | 1.674 | 0.378 | 0.126 | 3.144 |

Figure 4
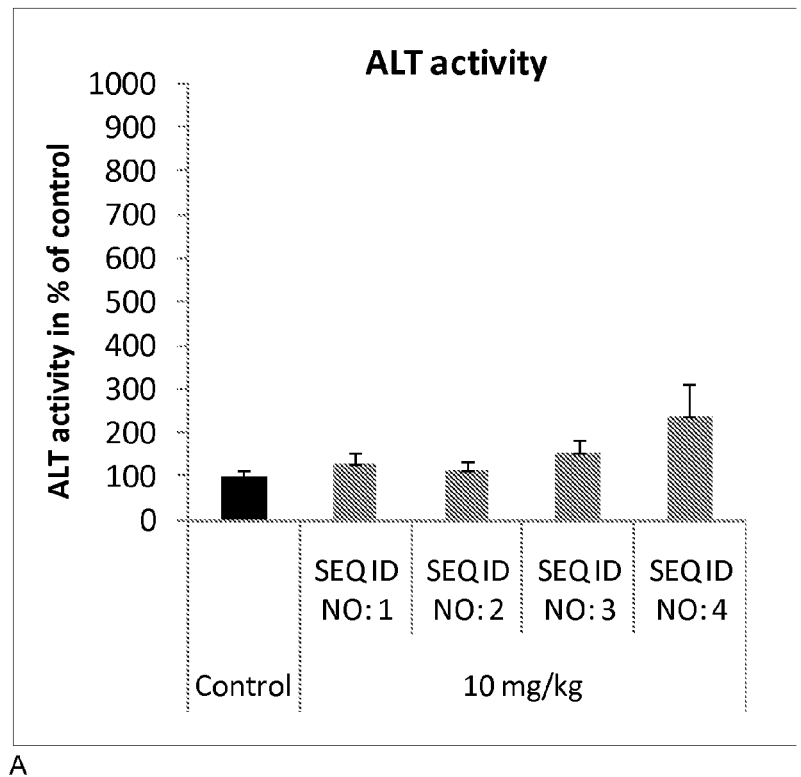
A
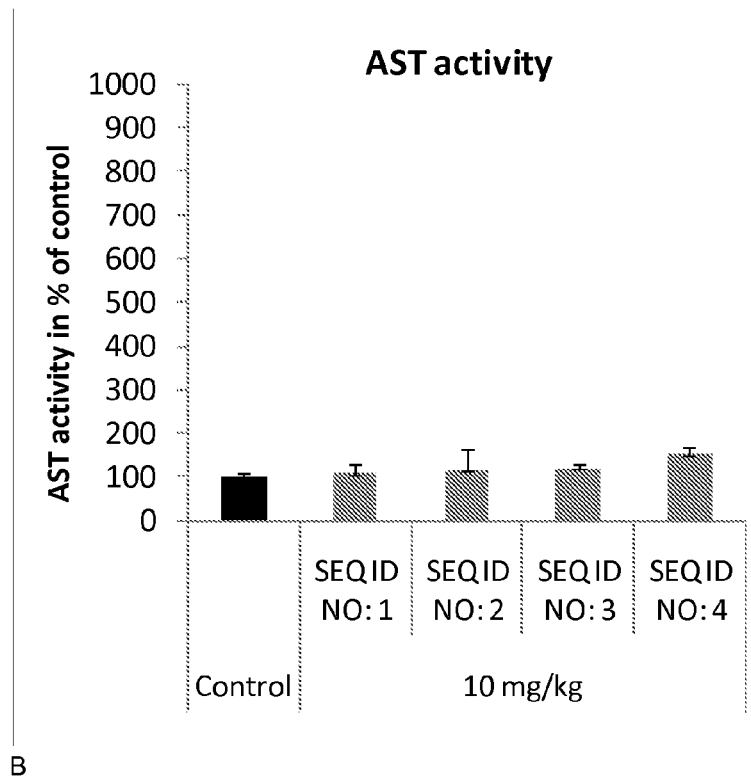
B

Figure 5

```
SEQ ID NO: 5
cagcgacgtc gaggcgctca tggttgcagg cgggcgccgc cgttcagttc agggtctgag      60
cctggaggag tgagccaggc agtgagactg gctcgggcgg gccgggacgc gtcgttgcag     120
cagcggctcc cagctcccag ccaggattcc gcgcgcccct tcacgcgccc tgctcctgaa     180
cttcagctcc tgcacagtcc tccccaccgc aaggctcaag gcgccgccgg cgtggaccgc     240
gcacggcctc taggtctcct cgccaggaca gcaacctctc cctggccct catgggcacc      300
gtcagctcca ggcggtcctg gtggccgctg ccactgctgc tgctgctgct gctgctcctg     360
ggtcccgcgg gcgcccgtgc gcaggaggac gaggacggcg actacgagga gctggtgcta     420
gccttgcgtt ccgaggagga cggcctggcc gaagcacccg agcacggaac cacagccacc     480
ttccaccgct gcgccaagga tccgtggagg ttgcctggca cctacgtggt ggtgctgaag     540
gaggagaccc acctctcgca gtcagagcgc actgcccgcc gcctgcaggc ccaggctgcc     600
cgccggggat acctcaccaa gatcctgcat gtcttccatg gccttcttcc tggcttcctg     660
gtgaagatga gtggcgacct gctggagctg gccttgaagt tgccccatgt cgactacatc     720
gaggaggact cctctgtctt tgcccagagc atcccgtgga acctggagcg gattacccct     780
ccacggtacc gggcggatga ataccagccc cccgacgag gcagcctggt ggaggtgtat      840
ctcctagaca ccagcataca gagtgaccac cgggaaatcg agggcagggt catggtcacc     900
gacttcgaga atgtgcccga ggaggacggg acccgcttcc acagacaggc cagcaagtgt     960
gacagtcatg gcacccacct ggcaggggtg gtcagcgcc gggatgccgg cgtggccaag    1020
ggtgccagca tgcgcagcct gcgcgtgctc aactgccaag ggaagggcac ggttagcggc    1080
accctcatag gcctggagtt tattcggaaa agccagctgg tccagcctgt ggggccactg    1140
gtggtgctgc tgcccctggc gggtgggtac agccgcgtcc tcaacgccgc ctgccagcgc    1200
ctggcgaggg ctggggtcgt gctggtcacc gctgccggca cttccgggga cgatgcctgc    1260
ctctactccc cagcctcagc tcccgaggtc atcacagttg gggccaccaa tgcccaagac    1320
cagccggtga ccctggggac tttggggacc aactttggcc gctgtgtgga cctctttgcc    1380
ccaggggagg acatcattgg tgcctccagc gactgcagca ctgctttgt gtcacagagt    1440
gggacatcac aggctgctgc ccacgtggct ggcattgcag ccatgatgct gtctgccgag    1500
ccggagctca ccctggccga gttgaggcag agactgatcg acttctctgc caaagatgtc    1560
atcaatgagg cctggttccc tgaggaccag cgggtactga cccccaacct ggtggccgcc    1620
ctgcccccca gcacccatgg ggcaggttgg cagctgtttt gcaggactgt atggtcagca    1680
cactcggggc ctacacggat ggccacagcc gtcgcccgct gcgccccaga tgaggagctg    1740
ctgagctgct ccagtttctc caggagtggg aagcggcggg gcgagcgcat ggaggcccaa    1800
gggggcaagc tggtctgccg ggcccacaac gctttggggg gtgagggtgt ctacgccatt    1860
gccaggtgct gcctgctacc ccaggccaac tgcagcgtcc acacagctcc accagctgag    1920
gccagcatgg ggacccgtgt ccactgccac caacagggcc acgtcctcac aggctgcagc    1980
tcccactggg aggtggagga ccttggcacc cacaagccgc ctgtgctgag gccacaggt    2040
cagcccaacc agtgcgtggg ccacaggag gccagcatcc acgcttcctg ctgccatgcc    2100
ccaggtctgg aatgcaaagt caaggagcat ggaatcccgg cccctcagga gcaggtgacc    2160
gtggcctgcg aggagggctg gaccctgact ggctgcagtg ccctccctgg gacctcccac    2220
gtcctggggg cctacgccgt agacaacacg tgtgtagtca ggagccggga cgtcagcact    2280
acaggcagca ccagcgaagg ggccgtgaca gccgttgcca tctgctgccg gagccggcac    2340
ctggcgcagg cctcccagga gctccagtga cagccccatc ccaggatggg tgtctgggga    2400
gggtcaaggg ctggggctga gctttaaaat ggttccgact tgtccctctc tcagccctcc    2460
atggcctggc acgaggggat ggggatgctt ccgcctttcc ggggctgctg gcctggccct    2520
tgagtggggc agcctccttg cctggaactc actcactctg ggtgcctcct ccccaggtgg    2580
aggtgccagg aagctccctc cctcactgtg gggcatttca ccattcaaac aggtcgagct    2640
gtgctcgggt gctgccagct gctcccaatg tgccgatgtc cgtgggcaga atgactttta    2700
ttgagctctt gttccgtgcc aggcattcaa tcctcaggtc tccaccaagg aggcaggatt    2760
cttcccatgg ataggggagg gggcggtagg ggctgcaggg acaaacatcg ttgggggtg     2820
agtgtgaaag gtgctgatgg ccctcatctc cagctaactg tggagaagcc cctgggggct    2880
ccctgattaa tggaggctta gctttctgga tggcatctag ccagaggctg agacaggtg     2940
cgcccctggt ggtcacaggc tgtgccttgg tttcctgagc cacctttact ctgctctatg    3000
ccaggctgtg ctagcaacac ccaaggtggc ctgcgggga gccatcacct aggactgact     3060
cggcagtgtg cagtggtgca tgcactgtct cagccaaccc gctccactac ccggcagggt    3120
acacattcgc accctactt cacagaggaa gaaacctgga ccagaggg gcgtgcctgc      3180
caagctcaca cagcaggaac tgagccagaa acgcagattg ggctggctct gaagccagac    3240
ctcttcttac ttcacccggc tgggctcctc atttttacgg gtaacagtga ggctgggaag    3300
gggaacacag accaggaagc tcggtgagtg atggcagaac gatgcctgca ggcatggaac    3360
ttttttccgtt atcacccagg cctgattcac tggcctggcg gagatgcttc taaggcatgg    3420
tcgggggaga gggccaacaa ctgtccctcc ttgagcacca gccccaccca agcaagcaga    3480
catttatctt ttgggtctgt cctctctgtt gccttttac agccaacttt tctagacctg    3540
ttttgctttt gtaacttgaa gatatttatt ctgggttttg tagcatttt attaatatgg    3600
tgactttta aaataaaaac aaacaaacgt tgtcct                              3636
```

ANTISENSE OLIGOMERS TARGETING PCSK9

REFERENCE TO A SEQUENCE LISTING SUBMITTED ELECTRONICALLY VIA EFS-WEB

The content of the electronically submitted sequence listing (Name: 2763.0290004Sequence_Listing.ascii.txt, Size: 14,535 bytes; and Date of Creation: Jun. 13, 2011) is herein incorporated by reference in its entirety.

FIELD OF INVENTION

The present invention relates to oligomeric compounds (oligomers) that target Proprotein Convertase Subtilisin/Kexin type 9 (PCSK9) PCSK9 mRNA in a cell, leading to reduced expression of PCSK9. Reduction of PCSK9 expression is beneficial for a range of medical disorders, such as hypercholesterolemia and related disorders.

RELATED CASES

The following related applications, U.S. provisional application 61/227,109, WO2008043753 and PCT/EP2007/060703 are hereby incorporated by reference in their entirety.

BACKGROUND

Proprotein convertase subtilisin/kexin type 9a (PCSK9) is a member of the proteinase K subfamily of subtilases. The PCSK9 gene (NARC-1) has been identified as a third locus involved in autosomal dominant hypercholesterolemia (ADH), characterised by high levels of low-density lipoprotein (LDL), xhantomas, and a high frequency of coronary heart disease. The other two loci being apolipoprotein-B (Apo-B) and the LDL receptor (LDLR). PCSK9 act as a natural inhibitor of the LDL-receptor pathway, and both genes are regulated by depletion of cholesterol cell content and statins via sterol regulatory element-binding protein (SREBP). PCSK9 mRNA and protein levels are regulated by food intake, insulin and cell cholesterol levels (Costet et al., J. Biol. Chem. January 2006).

The human NARC1 mRNA (cDNA) sequence, which encodes human PCSK9 is shown as SEQ ID NO: 5 (NCBI Acc. No. NM_174936).

The human PCSK9 polypeptide sequence (nascent) is NCBI Acc. No. NP_777596. The polypeptide has a signal peptide between residues 1-30, which is co-translationally cleaved to produce a proprotein (amino acids 31-692), which is subsequently cleaved by a protease to produce a mature protein corresponding to amino acids 83-692. A glycosylation site has been characterised at residue 533.

Park et al., (J. Biol. Chem. 279, pp 50630-50638, 2004) discloses that over-expression of PCSK9 reduced LDLR protein resulting in an increase in plasma LDL cholesterol, and suggests that an inhibitor of PCSK9 function may increase LDLR protein levels and enhance LDL clearance from plasma.

Rashid et al., (2005, PNAS 102, No 15, pp 5374-5379) discloses that knockout mice lacking PCSK9 manifest increased LDLR protein leading to an increased clearance of circulating lipoproteins and decreased plasma cholesterol levels, and suggests that inhibitors of PCSK9 may be useful for the treatment of hypercholesterolemia and that there may be synergy between inhibitors of PCSK9 and statins to enhance LDLRs and reduce plasma cholesterol.

WO01/57081 discloses the NARC-1 polynucleotide sequence and discloses that antisense nucleic acids can be designed using the NARC-1 polynucleotide sequence, and that such antisense nucleic acids may comprise modified nucleotides or bases, such as peptide nucleic acids.

WO2004/097047, which discloses two mutants of PCSK9 which are associated with ADH, suggests that antisense or RNAi of such PCSK9 mutants may be used for treatment of ADH.

The mainstay of atherosclerotic pharmacotherapy has been chronic therapy to prevent or slow the development of atherosclerotic plaques primarily by focusing on lowering LDL or "bad cholesterol" as a therapeutic endpoint. Statin therapy, for example, has greatly contributed to improved cardiovascular health; however, adverse effects such as rhabdomyolysis, remain an impediment. Furthermore, statins do little in an acute situation, for example, to reduce vulnerable, unstable atherosclerotic plaque during an ischemic episode. Acute treatment has largely relied on thrombolytics (such as tPA) and surgical intervention such a percutaneous transluminal coronary angioplasty (PTCA) and coronary artery bypass graft (CABG). While thrombolytics provide relief by decreasing or eliminating an occluding thrombus, they do not alter the underlying pathology. Interventions such as PTCA carry their own risks and are often unsuitable for patients in acute conditions. Hence current pharmacologic therapies do little to help patients once unstable plaque presents as a risk. (See, Newton and Krause 2002, Atherosclerosis S3:31-38).

Yet despite the improved understanding of the pathophysiology of myocardial infarction and developments in atherosclerotic pharmacotherapy, safe and effective treatment modalities which have a fast onset of action to allow for treatment in the acute phase, and which do not have serious side effects when used for long term treatment are still desired.

The compounds of the present invention are potent and non-toxic inhibitors of PCSK9, useful for in treatment of hypercholesterolemia and related disorders.

SUMMARY OF INVENTION

The invention provides an oligomer of between 10-50, such as 10-30 nucleotides in length which comprises a contiguous nucleotide sequence of a total of between 10-30 nucleotides, wherein said contiguous nucleotide sequence is at least 80% (e.g., 85%, 90%, 95%, 98%, 99% or 100%) homologous to a region corresponding to the reverse complement of a mammalian PCSK9 gene or mRNA, such as SEQ ID NO: 5 or naturally occurring variant thereof. Thus, for example, the oligomer hybridizes to a single stranded nucleic acid molecule having the sequence of a portion of SEQ ID NO: 5.

The invention provides an oligomer which consists or comprises of a contiguous nucleotide sequence selected from the group consisting of SEQ ID NO 8 and 9.

The invention provides an gapmer oligomer which consists or comprises of SEQ ID NO 13 and 14.

The invention provides an LNA gapmer oligomer which consists or comprises of SEQ ID NO 18 and 19.

The invention provides an LNA gapmer oligomer which consists or comprises of SEQ ID NO 3 and 4.

The invention provides an beta-D-oxy LNA gapmer oligomer consisting of SEQ ID NO 3.

The invention provides an beta-D-oxy LNA gapmer oligomer consisting of SEQ ID NO 4.

The invention provides for a conjugate comprising the oligomer according to the invention, and at least one non-nucleotide or non-polynucleotide moiety covalently attached to said oligomer.

The invention provides for a pharmaceutical composition comprising the oligomer or the conjugate according to the invention, and a pharmaceutically acceptable diluent, carrier, salt or adjuvant.

The invention provides for the oligomer or the conjugate according to invention, for use as a medicament, such as for the treatment of hypercholesterolemia and related disorders. Wherein the term "related disorders" when referring to hypercholesterolemia refers to one or more of the conditions selected from the group consisting of: atherosclerosis, hyperlipidemia, HDL/LDL cholesterol imbalance, dyslipidemias, e.g., familial combined hyperlipidemia (FCHL), acquired hyperlipidemia, statin-resistant hypercholesterolemia, coronary artery disease (CAD), and coronary heart disease (CHD).

The invention provides for the use of an oligomer or the conjugate according to the invention, for the manufacture of a medicament for the treatment of hypercholesterolemia and related disorders.

The invention provides for a method of treating hypercholesterolemia and related disorders, said method comprising administering an, e.g. effective dose of, an oligomer, a conjugate or a pharmaceutical composition according to the invention, to a patient suffering from, or likely to suffer from hypercholesterolemia and related disorders.

The invention provides for a method for the inhibition of PCSK9 in a cell which is expressing PCSK9, said method comprising administering an oligomer, or a conjugate according to the invention to said cell so as to effect the inhibition of PCSK9 in said cell.

BRIEF DESCRIPTION OF FIGURES

FIG. 1: PCSK9 mRNA expression in A) 15PC3 cells and B) HuH-7 cells after transfection with LNA oligonucleotides SEQ ID NOs 1-4 & 10. Data are normalised to GAPDH and presented relative to mock control as mean±STD.

FIG. 2: Table showing IC50 values for SEQ ID NO: 1-4 & 10 as measured in Huh-7 and 15PC3 cells.

FIG. 4: A) ALT and B) AST activities measured in serum at the end of the experiment (day 16). Mice were administered LNA oligonucleotide days 0, 3, 7, 10 and 14; sacrificed day 16. Data represent mean±std, n=5.

FIG. 5: SEQ ID NO: 5. Human PCSK9 mRNA

DETAILED DESCRIPTION OF INVENTION

The Oligomer

Figure 3:
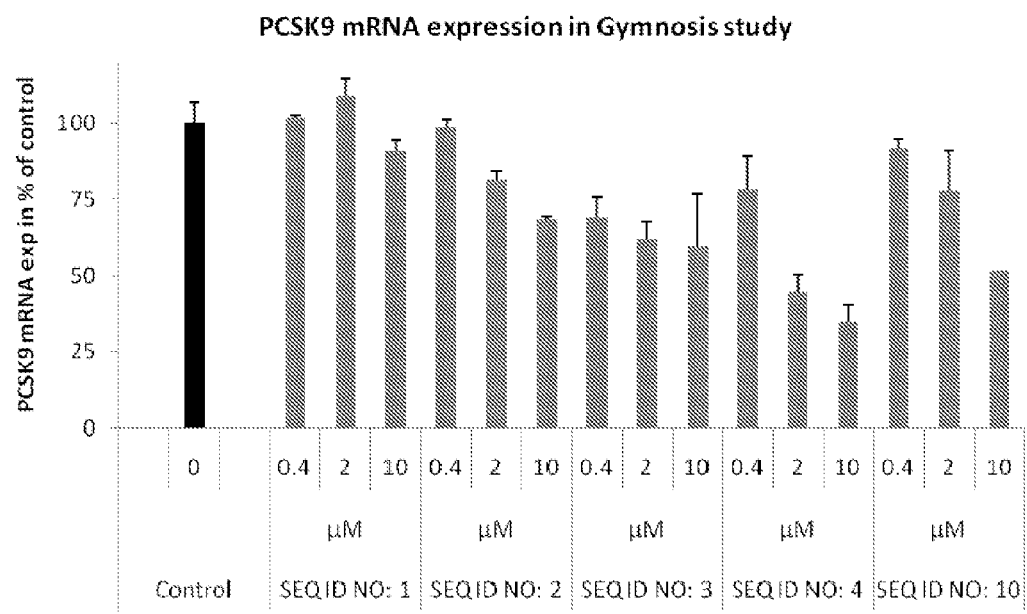
FIG. 3: PCSK9 mRNA expression in HepG2 cells 3 days after receiving LNA oligonucleotide in the media (0.4, 2 or 10 μM). QPCR data are normalised to the untreated control and presented as mean±std. (n=2).

The present invention employs oligomeric compounds (referred herein as oligomers), for use in modulating the function of nucleic acid molecules encoding mammalian PCSK9, such as the PCSK9 nucleic acid shown in SEQ ID NO: 5, and naturally occurring variants of such nucleic acid molecules encoding mammalian PCSK9. The term "oligomer" in the context of the present invention, refers to a molecule formed by covalent linkage of two or more nucleotides (i.e. an oligonucleotide). Herein, a single nucleotide (unit) may also be referred to as a monomer or unit. The oligomer consists or comprises of a contiguous nucleotide sequence of between 10-50, such as 10-30 nucleotides in length.

In various embodiments, the compound of the invention does not comprise RNA (units). It is preferred that the compound according to the invention is a linear molecule or is synthesised as a linear molecule. The oligomer is a single stranded molecule, and preferably does not comprise short regions of, for example, at least 3, 4 or 5 contiguous nucleotides, which are complementary to equivalent regions within the same oligomer (i.e. duplexes)—in this regards, the oligomer is not (essentially) double stranded. In some embodiments, the oligomer is essentially not double stranded, such as is not a siRNA. In various embodiments, the oligomer of the invention may consist entirely of the contiguous nucleotide region. Thus, the oligomer is not substantially self-complementary.

The Target

Suitably the oligomer of the invention is capable of down-regulating expression of the PCSK9 gene. In this regards, the oligomer of the invention can affect the expression of PCSK9, typically in a mammalian such as a human cell, such as a liver cell. In some embodiments, the oligomers of the invention bind to the target nucleic acid and affect of expression of at least 10% or 20% compared to the normal expression level, more preferably at least a 30%, 40%, 50%, 60%, 70%, 80%, 90% or 95% inhibition compared to the normal expression level. In some embodiments, such modulation is seen when using between 0.04 and 25 nM, such as between 0.8 and 20 nM concentration of the compound of the invention. In the same or a different embodiment, the inhibition of expression is less than 100%, such as less than 98% inhibition, less than 95% inhibition, less than 90% inhibition, less than 80% inhibition, such as less than 70% inhibition. Modulation of expression level may be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR. When measuring via mRNA levels, the level of down-regulation when using an appropriate dosage, such as between 0.04 and 25 nM, such as between 0.8 and 20 nM concentration, is, in some embodiments, typically to a level of between 10-20% the normal levels in the absence of the compound of the invention.

The invention therefore provides a method of down-regulating or inhibiting the expression of PCSK9 protein and/or mRNA in a cell which is expressing PCSK9 protein and/or mRNA, said method comprising administering the oligomer or conjugate according to the invention to said cell to down-regulating or inhibiting the expression of PCSK9 protein and/or mRNA in said cell. Suitably the cell is a mammalian cell such as a human cell. The administration may occur, in some embodiments, in vitro. The administration may occur, in some embodiments, in vivo.

The term "target nucleic acid", as used herein refers to the DNA or RNA encoding mammalian PCSK9 polypeptide, such as human PCSK9, such as SEQ ID NO: 5. PCSK9 encoding nucleic acids or naturally occurring variants thereof, and RNA nucleic acids derived therefrom, preferably mRNA, such as pre-mRNA, although preferably mature mRNA. In some embodiments, for example when used in research or diagnostics the "target nucleic acid" may be a cDNA or a synthetic oligonucleotide derived from the above DNA or RNA nucleic acid targets. The oligomer according to the invention is preferably capable of hybridising to the target nucleic acid. It will be recognised that SEQ ID NO: 5 is a cDNA sequence, and as such, corresponds to the mature mRNA target sequence, although uracil is replaced with thymidine in the cDNA sequences.

The term "naturally occurring variant thereof" refers to variants of the PCSK9 polypeptide of nucleic acid sequence which exist naturally within the defined taxonomic group, such as mammalian, such as mouse, monkey, and preferably human. Typically, when referring to "naturally occurring variants" of a polynucleotide the term also may encompass any allelic variant of the PCSK9 encoding genomic DNA which are found at the chromosome 4, at 4 C7 by chromosomal translocation or duplication, and the RNA, such as mRNA derived therefrom. "Naturally occurring variants" may also include variants derived from alternative splicing of the PCSK9 mRNA. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc.

Sequences

The oligomers comprise or consist of a contiguous nucleotide sequence which corresponds to the reverse complement of a nucleotide sequence present in SEQ ID NO: 5. Thus, the oligomer can comprise or consist of, a sequence selected from the group consisting of SEQ ID NOS: 6-9, wherein said oligomer (or contiguous nucleotide portion thereof) may optionally have one, two, or three mismatches against said selected sequence.

TABLE 1

Sequence Motifs

| SEQ ID NO | Length | Specificity | sequence |
|---|---|---|---|
| 6 | 12 | Mouse, human | 5'- GGTAGTGGAGCG -3' |
| 7 | 13 | Mouse, human | 5'- ACGTGTTGTCTAC -3' |

TABLE 1-continued

Sequence Motifs

| SEQ ID NO | Length | Specificity | sequence |
|---|---|---|---|
| 8 | 14 | Human | 5'- GCAACAGAGAGGAC -3' |
| 9 | 14 | Human | 5'- TGCTACAAAACCCA -3' |

The oligomer may comprise or consist of a contiguous nucleotide sequence which is fully complementary (perfectly complementary) to the equivalent region of a nucleic acid which encodes a mammalian PCSK9 (e.g., SEQ ID NO: 5). Thus, the oligomer can comprise or consist of an antisense nucleotide sequence.

However, in some embodiments, the oligomer may tolerate 1 or 2 mismatches, when hybridising to the target sequence and still sufficiently bind to the target to show the desired effect, i.e. down-regulation of the target. Mismatches may, for example, be compensated by increased length of the oligomer nucleotide sequence and/or an increased number of nucleotide analogues, such as LNA, present within the nucleotide sequence.

In some embodiments, the contiguous nucleotide sequence comprises no more than 2 mismatches when hybridizing to the target sequence, such as to the corresponding region of a nucleic acid which encodes a mammalian PCSK9.

In some embodiments, the contiguous nucleotide sequence comprises no more than a single mismatch when hybridizing to the target sequence, such as the corresponding region of a nucleic acid which encodes a mammalian PCSK9.

The nucleotide sequence of the oligomers of the invention or the contiguous nucleotide sequence is preferably at least 80% homologous to a corresponding sequence selected from the group consisting of SEQ ID NOS: 6-9, such as at least 85%, at least 90%, at least 91%, at least 92%, at least 93%, at least 94%, at least 95%, at least 96% homologous, such as 100% homologous (identical).

The nucleotide sequence of the oligomers of the invention or the contiguous nucleotide sequence is preferably at least 80% homologous to the reverse complement of a corresponding sequence present in SEQ ID NO: 5, such as at least 85%, at least 90%, at least 91%, at least 92% at least 93%, at least 94%, at least 95%, at least 96% homologous, such as 100% homologous (identical).

The nucleotide sequence of the oligomers of the invention or the contiguous nucleotide sequence is preferably at least 80% complementary to a sub-sequence present in SEQ ID NO: 5, such as at least 85%, at least 90%, at least 91%, at least 92%, at least 93%, at least 94%, at least 95%, at least 96% complementary, such as 100% complementary (perfectly complementary).

In some embodiments the oligomer (or contiguous nucleotide portion thereof) is selected from, or comprises, one of the sequences selected from the group consisting of SEQ ID NOS: 6, 7, 8, or 9, or a sub-sequence of at least 10 contiguous nucleotides thereof, wherein said oligomer (or contiguous nucleotide portion thereof) may optionally comprise one, two, or three mismatches when compared to the sequence.

In some embodiments the sub-sequence may consist of 11, 12, 13, or 14 contiguous nucleotides, such as between 12-14 nucleotides. Suitably, in some embodiments, the sub-sequence is of the same length as the contiguous nucleotide sequence of the oligomer of the invention.

However, it is recognised that, in some embodiments the nucleotide sequence of the oligomer may comprise additional 5' or 3' nucleotides, such as, independently, 1, 2, 3, 4 or 5 additional nucleotides 5' and/or 3', which are non-complementary to the target sequence. In this respect the oligomer of the invention, may, in some embodiments, comprise a contiguous nucleotide sequence which is flanked 5' and or 3' by additional nucleotides. In some embodiments the additional 5' or 3' nucleotides are naturally occurring nucleotides, such as DNA or RNA. In some embodiments, the additional 5' or 3' nucleotides may represent region D as referred to in the context of gapmer oligomers herein.

In some embodiments the oligomer according to the invention consists or comprises of a nucleotide sequence according to SEQ ID NO:6, or a sub-sequence of thereof.

In some embodiments the oligomer according to the invention consists or comprises of a nucleotide sequence according to SEQ ID NO:7, or a sub-sequence of thereof.

In some embodiments the oligomer according to the invention consists or comprises of a nucleotide sequence according to SEQ ID NO:8, or a sub-sequence of thereof.

In some embodiments the oligomer according to the invention consists or comprises of a nucleotide sequence according to SEQ ID NO:9, or a sub-sequence of thereof.

When determining "homology" between the oligomers of the invention (or contiguous nucleotide sequence) and the nucleic acid which encodes the mammalian PCSK9 or the reverse complement thereof, such as those disclosed herein, the determination of homology may be made by a simple alignment with the corresponding nucleotide sequence of the compound of the invention and the corresponding region of the nucleic acid which encodes the mammalian PCSK9 (or target nucleic acid), or the reverse complement thereof, and the homology is determined by counting the number of bases which align and dividing by the total number of contiguous nucleotides in the compound of the invention, and multiplying by 100. In such a comparison, if gaps exist, it is preferable that such gaps are merely mismatches rather than areas where the number of nucleotides within the gap differs between the nucleotide sequence of the invention and the target nucleic acid.

The terms "corresponding to" and "corresponds to" refer to the comparison between the nucleotide sequence of the oligomer or contiguous nucleotide sequence (a first sequence) and the equivalent contiguous nucleotide sequence of a further sequence selected from either i) a sub-sequence of the reverse complement of the nucleic acid target, such as the mRNA which encodes the PCSK9 protein, such as SEQ ID NO: 5, and/or ii) the sequence of nucleotides provided herein such as the group consisting of SEQ ID NOS: 6-9, or sub-sequence thereof. Nucleotide analogues are compared directly to their equivalent or corresponding nucleotides. A first sequence which corresponds to a further sequence under i) or ii) typically is identical to that sequence over the length of the first sequence (such as the contiguous nucleotide sequence) or, as described herein may, in some embodiments, is at least 80% homologous to a corresponding sequence, such as at least 85%, at least 90%, at least 91%, at least 92% at least 93%, at least 94%, at least 95%, at least 96% homologous, such as 100% homologous (identical).

The terms "corresponding nucleotide analogue" and "corresponding nucleotide" are intended to indicate that the nucleotide in the nucleotide analogue and the naturally occurring nucleotide are identical. For example, when the 2-deoxyribose unit of the nucleotide is linked to an adenine, the "corresponding nucleotide analogue" contains a pentose unit (different from 2-deoxyribose) linked to an adenine.

Length

The oligomers may comprise or consist of a contiguous nucleotide sequence of a total of between 10, 11, 12, 13, 14, 15, 16, 17, 18, 19, 20, 21, 22, 23, 24, 25, 26, 27, 28, 29 or 30 contiguous nucleotides in length.

In some embodiments, the oligomers comprise or consist of a contiguous nucleotide sequence of a total of between 10-22, such as 12-18, such as 13-17 or 12-16, such as 13, 14, 15, 16 contiguous nucleotides in length.

In some embodiments, the oligomers comprise or consist of a contiguous nucleotide sequence of a total of 10, 11, 12, 13, or 14 contiguous nucleotides in length.

In some embodiments, the oligomer according to the invention consists of no more than 22 nucleotides, such as no more than 20 nucleotides, such as no more than 18 nucleotides, such as 15, 16 or 17 nucleotides. In some embodiments the oligomer of the invention comprises less than 20 nucleotides.

Nucleotide Analogues

The term "nucleotide" as used herein, refers to a glycoside comprising a sugar moiety, a base moiety and a covalently linked group, such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogues" herein. Herein, a single nucleotide (unit) may also be referred to as a monomer or nucleic acid unit.

In field of biochemistry, the term "nucleoside" is commonly used to refer to a glycoside comprising a sugar moiety and a base moiety, and may therefore be used when referring to the nucleotide units, which are covalently linked by the internucleotide linkages between the nucleotides of the oligomer.

As one of ordinary skill in the art would recognise, the 5' nucleotide of an oligonucleotide does not comprise a 5' internucleotide linkage group, although may or may not comprise a 5' terminal group.

Non-naturally occurring nucleotides include nucleotides which have modified sugar moieties, such as bicyclic nucleotides or 2' modified nucleotides, such as 2' substituted nucleotides.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligonucleotide, i.e. have no functional effect on the way the oligonucleotide works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity to the target and/or increased resistance to intracellular nucleases and/or increased ease of transport into the cell. Specific examples of nucleoside analogues are described by e.g. Freier & Altmann; *Nucl. Acid Res.,* 1997, 25, 4429-4443 and Uhlmann; *Curr. Opinion in Drug Development,* 2000, 3(2), 293-213, and in Scheme 1:

Scheme 1

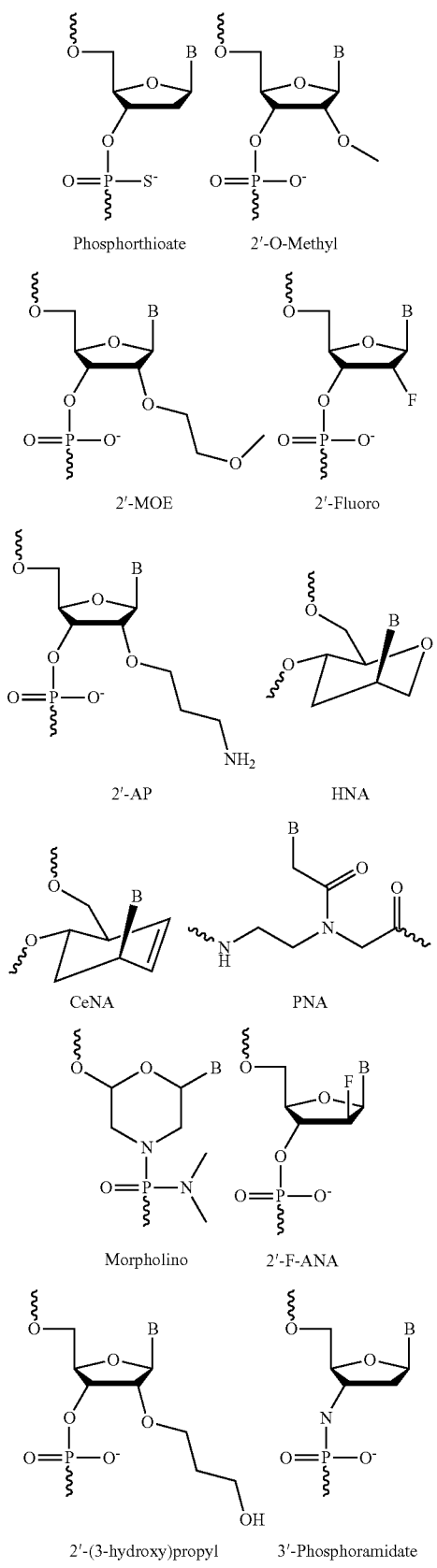

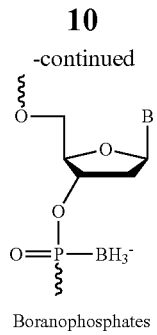

Boranophosphates

The oligomer may thus comprise or consist of a simple sequence of natural occurring nucleotides—preferably 2'-deoxynucleotides (referred to here generally as "DNA"), but also possibly ribonucleotides (referred to here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Examples of suitable and preferred nucleotide analogues are provided by PCT/DK2006/000512 or are referenced therein.

Incorporation of affinity-enhancing nucleotide analogues in the oligomer, such as LNA or 2'-substituted sugars, can allow the size of the specifically binding oligomer to be reduced, and may also reduce the upper limit to the size of the oligomer before non-specific or aberrant binding takes place.

In some embodiments the oligomer comprises at least 2 nucleotide analogues. In some embodiments, the oligomer comprises from 3-8 nucleotide analogues, e.g. 6 or 7 nucleotide analogues. In the by far most preferred embodiments, at least one of said nucleotide analogues is a locked nucleic acid (LNA); for example at least 3 or at least 4, or at least 5, or at least 6, or at least 7, or 8, of the nucleotide analogues may be LNA. In some embodiments all the nucleotides analogues may be LNA.

It will be recognised that when referring to a preferred nucleotide sequence motif or nucleotide sequence, which consists of only nucleotides, the oligomers of the invention which are defined by that sequence may comprise a corresponding nucleotide analogue in place of one or more of the nucleotides present in said sequence, such as LNA units or other nucleotide analogues, which raise the duplex stability/ $T_m$ of the oligomer/target duplex (i.e. affinity enhancing nucleotide analogues).

In some embodiments, any mismatches between the nucleotide sequence of the oligomer and the target sequence are preferably found in regions outside the affinity enhancing nucleotide analogues, such as region B as referred to herein, and/or region D as referred to herein, and/or at the site of non modified such as DNA nucleotides in the oligonucleotide, and/or in regions which are 5' or 3' to the contiguous nucleotide sequence.

Examples of such modification of the nucleotide include modifying the sugar moiety to provide a 2'-substituent group or to produce a bridged (locked nucleic acid) structure which enhances binding affinity and may also provide increased nuclease resistance.

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments the nucleotide analogues present within the oligomer of the invention (such as in regions A and C mentioned herein) are independently selected from, for example: 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'MOE units. In some embodiments there is only one of the above types of nucleotide analogues present in the oligomer of the invention, or contiguous nucleotide sequence thereof.

In some embodiments the nucleotide analogues are 2'-O-methoxyethyl-RNA (2'MOE), 2'-fluoro-DNA monomers or LNA nucleotide analogues, and as such the oligonucleotide of the invention may comprise nucleotide analogues which are independently selected from these three types of analogue, or may comprise only one type of analogue selected from the three types. In some embodiments at least one of said nucleotide analogues is 2'-MOE-RNA, such as 2, 3, 4, 5, 6, 7, 8, 9 or 10 2'-MOE-RNA nucleotide units. In some embodiments at least one of said nucleotide analogues is 2'-fluoro DNA, such as 2, 3, 4, 5, 6, 7, 8, 9 or 10 2'-fluoro-DNA nucleotide units.

In some embodiments, the oligomer according to the invention comprises at least one Locked Nucleic Acid (LNA) unit, such as 1, 2, 3, 4, 5, 6, 7, or 8 LNA units, such as between 3-7 or 4 to 8 LNA units, or 3, 4, 5, 6 or 7 LNA units. In some embodiments, all the nucleotide analogues are LNA. In some embodiments, the oligomer may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5' methyl-Cytosine. In some embodiments of the invention, the oligomer may comprise both LNA and DNA units. Preferably the combined total of LNA and DNA units is 10-25, preferably 10-20, even more preferably 12-16. In some embodiments of the invention, the nucleotide sequence of the oligomer, such as the contiguous nucleotide sequence consists of at least one LNA and the remaining nucleotide units are DNA units. In some embodiments the oligomer comprises only LNA nucleotide analogues and naturally occurring nucleotides (such as RNA or DNA, most preferably DNA nucleotides), optionally with modified internucleotide linkages such as phosphorothioate.

The term "nucleobase" refers to the base moiety of a nucleotide and covers both naturally occurring a well as non-naturally occurring variants. Thus, "nucleobase" covers not only the known purine and pyrimidine heterocycles but also heterocyclic analogues and tautomeres thereof.

Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments, at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA" refers to a bicyclic nucleotide analogue, known as "Locked Nucleic Acid". It may refer to an LNA monomer, or, when used in the context of an "LNA oligonucleotide", LNA refers to an oligonucleotide containing one or more such bicyclic nucleotide analogues. LNA nucleotides are characterised by the presence of a biradical 'bridge' between C2' and C4' of the ribose sugar ring—for example as shown as the biradical $R^{4*}$-$R^{2*}$ as described below.

The LNA used in the oligonucleotide compounds of the invention preferably has the structure of the general formula I

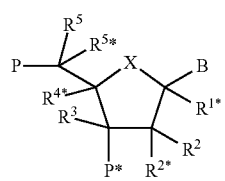

Formula 1 wherein for all chiral centers, asymmetric groups may be found in either R or S orientation;

wherein X is selected from —O—, —S—, —N($R^{N*}$)—, —C($R^6R^{6*}$)—, such as, in some embodiments —O—;

B is selected from hydrogen, optionally substituted $C_{1-4}$-alkoxy, optionally substituted $C_{1-4}$-alkyl, optionally substituted $C_{1-4}$-acyloxy, nucleobases including naturally occurring and nucleobase analogues, DNA intercalators, photochemically active groups, thermochemically active groups, chelating groups, reporter groups, and ligands;

P designates an internucleotide linkage to an adjacent monomer, or a 5'-terminal group, such internucleotide linkage or 5'-terminal group optionally including the substituent $R^5$ or equally applicable the substituent $R^{5*}$;

P* designates an internucleotide linkage to an adjacent monomer, or a 3'-terminal group;

$R^{4*}$ and $R^{2*}$ together designate a biradical consisting of 1-4 groups/atoms selected from —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, optionally substituted $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation, and;

each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene; wherein $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof. For all chiral centers, asymmetric groups may be found in either R or S orientation.

In some embodiments, $R^{4*}$ and $R^{2*}$ together designate a biradical consisting of a groups selected from the group consisting of $C(R^aR^b)$—$C(R^aR^b)$—, $C(R^aR^b)$—O—, $C(R^aR^b)$—$NR^a$—, $C(R^aR^b)$—S—, and $C(R^aR^b)$—C($R^aR^b$)—O—, wherein each $R^a$ and $R^b$ may optionally be independently selected. In some embodiments, $R^a$ and $R^b$ may be, optionally independently selected from the group consisting of hydrogen and $C_{1-6}$alkyl, such as methyl, such as hydrogen.

In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$, $R^5$, $R^{5*}$ are hydrogen.

In some embodiments, $R^{1*}$, $R^2$, $R^3$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$ are hydrogen.

In some embodiments, $R^5$ and $R^{5*}$ are each independently selected from the group consisting of H, —$CH_3$, —$CH_2$—$CH_3$, —$CH_2$—O—$CH_3$, and —CH=$CH_2$. Suitably in some embodiments, either $R^5$ or $R^{5*}$ are hydrogen, where as the other group ($R^5$ or $R^{5*}$ respectively) is selected from the group consisting of $C_{1-5}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl or substituted acyl (—C(=O)—); wherein each substituted group is mono or poly substituted with substituent groups independently selected from halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $OJ_1$, $SJ_1$, $NJ_1J_2$, $N_3$, $COOJ_1$, CN, O—C(=O)$NJ_1J_2$, N(H)C(=NH)$NJ_1J_2$ or N(H)C(=X)N(H)$J_2$ wherein X is O or S; and each $J_1$ and $J_2$ is, independently, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ aminoalkyl, substituted $C_{1-6}$ aminoalkyl or a protecting group. In some embodiments either $R^5$ or $R^{5*}$ is substituted $C_{1-6}$alkyl. In some embodiments either $R^5$ or $R^{5*}$ is substituted methylene wherein preferred substituent groups include one or more groups independently selected from F, $NJ_1J_2$, $N_3$, CN, $OJ_1$, $SJ_1$, O—C(=O)$NJ_1J_2$, N(H)C(=NH) $NJ_1J_2$ or N(H)C(O)N(H)$J_2$. In some embodiments each $J_1$ and $J_2$ is, independently H or $C_{1-6}$alkyl. In some embodiments either $R^5$ or $R^{5*}$ is methyl, ethyl or methoxymethyl. In some embodiments either $R^5$ or $R^{5*}$ is methyl. In a further embodiment either $R^5$ or $R^{5*}$ is ethylenyl. In some embodiments either $R^5$ or $R^{5*}$ is substituted acyl. In some embodiments either $R^5$ or $R^{5*}$ is C(=O)$NJ_1J_2$. For all chiral centers, asymmetric groups may be found in either R or S orientation. Such 5' modified bicyclic nucleotides are disclosed in WO 2007/134181, which is hereby incorporated by reference in its entirety.

In some embodiments B is a nucleobase, including nucleobase analogues and naturally occurring nucleobases, such as a purine or pyrimidine, or a substituted purine or substituted pyrimidine, such as a nucleobase referred to herein, such as a nucleobase selected from the group consisting of adenine, cytosine, thymine, adenine, uracil, and/or a modified or substituted nucleobase, such as 5-thiazolo-uracil, 2-thio-uracil, 5-propynyl-uracil, 2' thio-thymine, 5-methyl cytosine, 5-thiozolo-cytosine, 5-propynyl-cytosine, and 2,6-diaminopurine.

In some embodiments, $R^{4*}$ and $R^{2*}$ together designate a biradical selected from —$C(R^aR^b)$—O—, —$C(R^aR^b)$—C($R^cR^d$)—O—, —$C(R^aR^b)$—$C(R^cR^d)$—$C(R^eR^f)$—O—, —$C(R^aR^b)$—O—$C(R^cR^d)$—, —$C(R^aR^b)$—O—$C(R^cR^d)$—O—, —$C(R^aR^b)$—$C(R^cR^d)$—, —$C(R^aR^b)$—$C(R^cR^d)$—$C(R^eR^f)$—, —$C(R^a)$=$C(R^b)$—$C(R^cR^d)$—, —$C(R^aR^b)$—N($R^c$)—, —$C(R^aR^b)$—$C(R^cR^d)$—N($R^c$)—, —$C(R^aR^b)$—N($R^c$)—O—, and —$C(R^aR^b)$—S—, —$C(R^aR^b)$—$C(R^cR^d)$—S—, wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$). For all chiral centers, asymmetric groups may be found in either R or S orientation.

In a further embodiment $R^{4*}$ and $R^{2*}$ together designate a biradical (bivalent group) selected from —$CH_2$—O—, —$CH_2$—S—, —$CH_2$—NH—, —$CH_2$—N($CH_3$)—, —$CH_2$—$CH_2$—O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —CH=CH—$CH_2$—, —$CH_2$—O—$CH_2$—O—, —$CH_2$—NH—O—, —$CH_2$—N($CH_3$)—O—, —$CH_2$—O—$CH_2$—, —CH($CH_3$)—O—, and —CH($CH_2$—O—$CH_3$)—O—, and/or, —$CH_2$—$CH_2$—, and —CH=CH—For all chiral centers, asymmetric groups may be found in either R or S orientation.

In some preferred embodiments, $R^{4*}$ and $R^{2*}$ together designate the biradical —O—CH($CH_2OCH_3$)— (2'O-methoxyethyl bicyclic nucleic acid—Seth at al., 2010, J. Org. Chem)—in either the R- or S-configuration.

In some preferred embodiments, $R^{4*}$ and $R^{2*}$ together designate the biradical —O—CH($CH_2CH_3$)— (2'O-ethyl bicyclic nucleic acid—Seth at al., 2010, J. Org. Chem)—in either the R- or S-configuration.

In some preferred embodiments, $R^{4*}$ and $R^{2*}$ together designate the biradical —O—CH(CH$_3$)—.—in either the R- or S-configuration. In some embodiments, $R^{4*}$ and $R^{2*}$ together designate the biradical C($R^aR^b$)—N($R^c$)—O—, wherein $R^a$ and $R^b$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen, and; wherein $R^c$ is selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ together designate the biradical C($R^aR^b$)—O—C($R^cR^d$)—O—, wherein $R^a$, $R^b$, $R^c$, and $R^d$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$alkynyl, $C_{1-6}$ alkoxyl, substituted $C_{1-6}$alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ form the biradical —CH(Z)—O—, wherein Z is selected from the group consisting of $C_{1-6}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl, acyl, substituted acyl, substituted amide, thiol or substituted thio; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, OC(=X)$J_1$, OC(=X)$NJ_1J_2$, $NJ^3$C(=X)$NJ_1J_2$ and CN, wherein each $J_1$, $J_2$ and $J_3$ is, independently, H or $C_{1-6}$ alkyl, and X is O, S or $NJ_1$. In some embodiments Z is $C_{1-6}$ alkyl or substituted $C_{1-6}$ alkyl. In some embodiments Z is methyl. In some embodiments Z is substituted $C_{1-6}$ alkyl. In some embodiments said substituent group is $C_{1-6}$ alkoxy. In some embodiments Z is CH$_3$OCH$_2$—. For all chiral centers, asymmetric groups may be found in either R or S orientation. Such bicyclic nucleotides are disclosed in U.S. Pat. No. 7,399,845 which is hereby incorporated by reference in its entirety. In some embodiments, $R^{1*}$, $R^2$, $R^3$, $R^5$, $R^{5*}$ are hydrogen. In some embodiments, $R^{1*}$, $R^2$, $R^{3*}$ are hydrogen, and one or both of $R^5$, $R^{5*}$ may be other than hydrogen as referred to above and in WO 2007/134181.

In some embodiments, $R^{4*}$ and $R^{2*}$ together designate a biradical which comprise a substituted amino group in the bridge such as consist or comprise of the biradical —CH$_2$—N($R^c$)—, wherein $R^c$ is $C_{1-12}$ alkyloxy. In some embodiments $R^{4*}$ and $R^{2*}$ together designate a biradical —Cq$_3$q$_4$-NOR—, wherein q$_3$ and q$_4$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, alkoxyl, substituted $C_{1-6}$alkoxyl, acyl, substituted acyl, $C_{1-6}$ aminoalkyl or substituted $C_{1-6}$ aminoalkyl; wherein each substituted group is, independently, mono or poly substituted with substituent groups independently selected from halogen, $OJ_1$, $SJ_1$, $NJ_1J_2$, $COOJ_1$, CN, O—C(=O)$NJ_1J_2$, N(H)C(=NH)$NJ_1J_2$ or N(H)C(=X=N(H)$J_2$ wherein X is O or S; and each of $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group. For all chiral centers, asymmetric groups may be found in either R or S orientation. Such bicyclic nucleotides are disclosed in WO2008/150729 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$alkoxyl, acyl, substituted acyl, $C_{1-6}$-aminoalkyl or substituted $C_{1-6}$-aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181. In some embodiments $R^{4*}$ and $R^{2*}$ together designate a biradical (bivalent group) C($R^aR^b$)—O—, wherein $R^a$ and $R^b$ are each independently halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$; or $R^a$ and $R^b$ together are =C(q$_3$)(q$_4$); q$_3$ and q$_4$ are each, independently, H, halogen, $C_1$-$C_{12}$alkyl or substituted $C_1$-$C_{12}$ alkyl; each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ or N(H)C(=S)$NJ_1J_2$ and; each $J_1$ and $J_2$ is, independently, H, $C1$-$C_6$ alkyl, substituted $C1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C1$-$C_6$ aminoalkyl, substituted $C1$-$C_6$ aminoalkyl or a protecting group. Such compounds are disclosed in WO2009006478A, hereby incorporated in its entirety by reference.

In some embodiments, $R^{4*}$ and $R^{2*}$ form the biradical -Q-, wherein Q is C(q$_1$)(q$_2$)C(q$_3$)(q$_4$), C(q$_1$)=C(q$_3$), C[=C(q$_1$)(q$_2$)]-C(q$_3$)(q$_4$) or C(q$_1$)(q$_2$)—C[=C(q$_3$)(q$_4$)]; q$_1$, q$_2$, q$_3$, q$_4$ are each independently. H, halogen, $C_{1-12}$ alkyl, substituted $C_{1-12}$ alkyl, $C_{2-12}$ alkenyl, substituted $C_{1-12}$ alkoxy, $OJ_1$, $SJ_1$, $SOJ_1$, $SO_2J_1$, $NJ_1J_2$, $N_3$, CN, C(=O)$OJ_1$, C(=O)—$NJ_1J_2$, C(=O) $J_1$, —C(=O)$NJ_1J_2$, N(H)C(=NH)$NJ_1J_2$, N(H)C (=O)$NJ_1J_2$ or N(H)C(=S)$NJ_1J_2$; each $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group; and, optionally wherein when Q is C(q$_1$)(q$_2$)(q$_3$)(q$_4$) and one of q$_3$ or q$_4$ is CH$_3$ then at least one of the other of q$_3$ or q$_4$ or one of q$_1$ and q$_2$ is other than H. In some embodiments, $R^{1*}$, $R^2$, $R^3$, $R^5$, $R^{5*}$ are hydrogen. For all chiral centers, asymmetric groups may be found in either R or S orientation. Such bicyclic nucleotides are disclosed in WO2008/154401 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$-aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181 or WO2009/067647 (alpha-L-bicyclic nucleic acids analogs).

In some embodiments the LNA used in the oligonucleotide compounds of the nvention preferably has the structure of the general formula II:

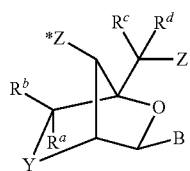

Formula II wherein Y is selected from the group consisting of —O—, —$CH_2$O—, —S—, —NH—, N($R^e$) and/or —$CH_2$—; Z and Z* are independently selected among an internucleotide linkage, $R^H$, a terminal group or a protecting group; B constitutes a natural or non-natural nucleotide base moiety (nucleobase), and $R^H$ is selected from hydrogen and $C_{1-4}$-alkyl; $R^a$, $R^bR^c$, $R^d$ and $R^e$ are, optionally independently, selected from the group consisting of hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl) amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$); and $R^H$ is selected from hydrogen and $C_{1-4}$-alkyl. In some embodiments $R^a$, $R^bR^c$, $R^d$ and $R^e$ are, optionally independently, selected from the group consisting of hydrogen and $C_{1-6}$alkyl, such as methyl. For all chiral centers, asymmetric groups may be found in either R or S orientation, for example, two exemplary stereochemical isomers include the beta-D and alpha-L isoforms, which may be illustrated as follows:

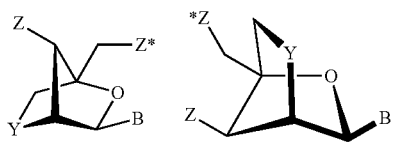

Specific exemplary LNA units are shown below:

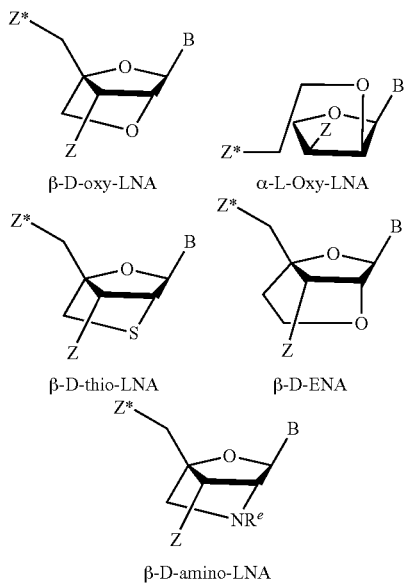

β-D-oxy-LNA α-L-Oxy-LNA

β-D-thio-LNA β-D-ENA

β-D-amino-LNA

The term "thio-LNA" comprises a locked nucleotide in which Y in the general formula above is selected from S or —$CH_2$—S—. Thio-LNA can be in both beta-D and alpha-L-configuration.

The term "amino-LNA" comprises a locked nucleotide in which Y in the general formula above is selected from —N(H)—, N(R)—, $CH_2$—N(H)—, and —$CH_2$—N(R)— where R is selected from hydrogen and $C_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —$CH_2$—O— (where the oxygen atom of —$CH_2$—O— is attached to the 2'-position relative to the base B). $R^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

RNAse Recruitment

It is recognised that an oligomeric compound may function via non RNase mediated degradation of target mRNA, such as by steric hindrance of translation, or other methods, however, the preferred oligomers of the invention are capable of recruiting an endoribonuclease (RNase), such as RNase H.

It is preferable that the oligomer, or contiguous nucleotide sequence, comprises of a region of at least 6, such as at least 7 consecutive nucleotide units, such as at least 8 or at least 9 consecutive nucleotide units (residues), including 7, 8, 9, 10, 11, 12, 13, 14, 15 or 16 consecutive nucleotides, which, when formed in a duplex with the complementary target RNA is capable of recruiting RNase. The contiguous sequence which is capable of recruiting RNAse may be region B as referred to in the context of a gapmer as described herein. In some embodiments the size of the contiguous sequence which is capable of recruiting RNAse, such as region B, may be higher, such as 10, 11, 12, 13, 14, 15, 16, 17, 18, 19 or 20 nucleotide units.

EP 1 222 309 provides in vitro methods for determining RNaseH activity, which may be used to determine the ability to recruit RNaseH. A oligomer is deemed capable of recruiting RNase H if, when provided with the complementary RNA target, it has an initial rate, as measured in pmol/l/min, of at least 1%, such as at least 5%, such as at least 10% or, more than 20% of the equivalent DNA only oligonucleotide, with no 2' substitutions, with phosphorothioate linkage groups between all nucleotides in the oligonucleotide, using the methodology provided by Example 91-95 of EP 1 222 309.

In some embodiments, an oligomer is deemed essentially incapable of recruiting RNaseH if, when provided with the complementary RNA target, and RNaseH, the RNaseH initial rate, as measured in pmol/l/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

In other embodiments, an oligomer is deemed capable of recruiting RNaseH if, when provided with the complementary RNA target, and RNaseH, the RNaseH initial rate, as measured in pmol/l/min, is at least 20%, such as at least 40%, such as at least 60%, such as at least 80% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

Typically the region of the oligomer which forms the consecutive nucleotide units which, when formed in a duplex with the complementary target RNA is capable of recruiting RNase consists of nucleotide units which form a DNA/RNA like duplex with the RNA target—and include both DNA units and LNA units which are in the alpha-L configuration, particularly preferred being alpha-L-oxy LNA.

The oligomer of the invention may comprise a nucleotide sequence which comprises both nucleotides and nucleotide analogues, and may be in the form of a gapmer, a headmer or a mixmer.

A headmer is defined by a contiguous stretch of non-RNase recruiting nucleotide analogues at the 5'-end followed by a contiguous stretch of DNA or modified nucleotide units recognizable and cleavable by the RNase towards the 3'-end (such as at least 7 such nucleotides), and a tailmer is defined by a contiguous stretch of DNA or modified nucleotides recognizable and cleavable by the RNase at the 5'-end (such as at least 7 such nucleotides), followed by a contiguous stretch of non-RNase recruiting nucleotide analogues towards the 3'-end. Other chimeras according to the invention, called mixmers consisting of an alternate composition of DNA or modified nucleotides recognizable and cleavable by RNase and non-RNase recruiting nucleotide analogues. Some nucleotide analogues may also be able to mediate RNaseH binding and cleavage. Since α-L-LNA recruits RNaseH activity to a certain extent, smaller gaps of DNA or modified nucleotides recognizable and cleavable by the RNaseH for the gapmer construct might be required, and more flexibility in the mixmer construction might be introduced.

Gapmer Design

Preferably, the oligomer of the invention is a gapmer. A gapmer oligomer is an oligomer which comprises a contiguous stretch of nucleotides which is capable of recruiting an RNAse, such as RNAseH, such as a region of at least 6 or 7 DNA nucleotides, referred to herein in as region B, wherein region B is flanked both 5' and 3' by regions of affinity enhancing nucleotide analogues, such as between 1-6 nucleotide analogues 5' and 3' to the contiguous stretch of nucleotides which is capable of recruiting RNAse—these regions are referred to as regions A and C respectively.

In some embodiments, the nucleotides which are capable of recruiting RNAse are selected from the group consisting of DNA nucleotides, alpha-L-LNA nucleotides, C4' alkylated DNA. (see PCT/EP2009/050349 hereby incorporated by reference), and UNA nucleotides (see Fluiter et al., Mol. Biosyst., 2009, 10, 1039 hereby incorporated by reference). In some embodiments, region B consists of a contiguous length of at least 6 or 7 DNA nucleotides, or nucleotides selected from the group consisting of DNA and alpha-L-LNA.

Preferably the gapmer comprises a (poly)nucleotide sequence of formula (5' to 3'), A-B-C, or optionally A-B-C-D or D-A-B-C, wherein; region A (5' region) consists or comprises of at least one nucleotide analogue, such as at least one LNA unit, such as between 1-6 nucleotide analogues, such as LNA units, and; region B consists or comprises of at least five consecutive nucleotides which are capable of recruiting RNAse (when formed in a duplex with a complementary RNA molecule, such as the mRNA target), such as DNA nucleotides, and; region C (3' region) consists or comprises of at least one nucleotide analogue, such as at least one LNA unit, such as between 1-6 nucleotide analogues, such as LNA units, and; region D, when present consists or comprises of 1, 2 or 3 nucleotide units, such as DNA nucleotides.

In some embodiments, region A consists of 1, 2, 3, 4, 5 or 6 nucleotide analogues, such as LNA units, such as between 2-5 nucleotide analogues, such as 2-5 LNA units, such as 3 or 4 nucleotide analogues, such as 3 or 4 LNA units; and/or region C consists of 1, 2, 3, 4, 5 or 6 nucleotide analogues, such as LNA units, such as between 2-5 nucleotide analogues, such as 2-5 LNA units, such as 3 or 4 nucleotide analogues, such as 3 or 4 LNA units.

In some embodiments B consists or comprises of 5, 6, 7, 8, 9, 10, 11 or 12 consecutive nucleotides which are capable of recruiting RNAse, or between 6-10, or between 7-9, such as 8 consecutive nucleotides which are capable of recruiting RNAse. In some embodiments region B consists or comprises at least one DNA nucleotide unit, such as 1-12 DNA units, preferably between 4-12 DNA units, more preferably between 6-10 DNA units, such as between 7-10 DNA units, most preferably 8, 9 or 10 DNA units.

In some embodiments region A consist of 3 or 4 nucleotide analogues, such as LNA, region B consists of 7, 8, 9 or 10 DNA units, and region C consists of 3 or 4 nucleotide analogues, such as LNA. Such designs include (A-B-C) 3-10-3, 3-10-4, 4-10-3, 3-9-3, 3-9-4, 4-9-3, 3-8-3, 3-8-4, 4-8-3, 3-7-3, 3-7-4, 4-7-3, and may further include region D, which may have one or 2 nucleotide units, such as DNA units.

Further gapmer designs are disclosed in WO2004/046160 and are hereby incorporated by reference.

U.S. provisional application, 60/977,409, hereby incorporated by reference, refers to 'shortmer' gapmer oligomers, which, in some embodiments may be the gapmer oligomer according to the present invention.

In some embodiments the oligomer is consisting of a contiguous nucleotide sequence of a total of 10, 11, 12, 13 or 14 nucleotide units, wherein the contiguous nucleotide sequence is of formula (5'-3'), A-B-C, or optionally A-B-C-D or D-A-B-C, wherein; A consists of 1, 2 or 3 nucleotide analogue units, such as LNA units; B consists of 7, 8 or 9 contiguous nucleotide units which are capable of recruiting RNAse when formed in a duplex with a complementary RNA molecule (such as a mRNA target); and C consists of 1, 2 or 3 nucleotide analogue units, such as LNA units. When present, D consists of a single DNA unit.

In some embodiments A consists of 1 LNA unit. In some embodiments A consists of 2 LNA units. In some embodiments A consists of 3 LNA units. In some embodiments C consists of 1 LNA unit. In some embodiments C consists of 2 LNA units. In some embodiments C consists of 3 LNA units. In some embodiments B consists of 7 nucleotide units. In some embodiments B consists of 8 nucleotide units. In some embodiments B consists of 9 nucleotide units. In some embodiments B comprises of between 1-9 DNA units, such as 2, 3, 4, 5, 6, 7 or 8 DNA units. In some embodiments B consists of DNA units. In some embodiments B comprises of at least one LNA unit which is in the alpha-L configuration, such as 2, 3, 4, 5, 6, 7, 8 or 9 LNA units in the alpha-L-configuration. In some embodiments B comprises of at least one alpha-L-oxy LNA unit or wherein all the LNA units in the alpha-L-configuration are alpha-L-oxy LNA units. In some embodiments the number of nucleotides present in A-B-C are selected from the group consisting of (nucleotide analogue units—region B—nucleotide analogue units): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1. In some embodiments the number of nucleotides in A-B-C are selected from the group consisting of: 2-7-1, 1-7-2, 2-7-2, 3-7-3, 2-7-3, 3-7-2, 3-7-4, and 4-7-3. In some embodiments both A and C consists of two LNA units each, and B consists of 8 or 9 nucleotide units, preferably DNA units.

In one preferred embodiment, the number of nucleotides present are those shown in SEQ ID NO's: 1, 2, 3, or 4.

Internucleotide Linkages

The terms "linkage group" or "internucleotide linkage" are intended to mean a group capable of covalently coupling together two nucleotides. Specific and preferred examples include phosphate groups and phosphorothioate groups.

The nucleotides of the oligomer of the invention or contiguous nucleotides sequence thereof are coupled together via linkage groups. Suitably each nucleotide is linked to the 3' adjacent nucleotide via a linkage group.

Suitable internucleotide linkages include those listed within PCT/DK2006/000512, for example the internucleotide linkages listed on the first paragraph of page 34 of PCT/DK2006/000512 (hereby incorporated by reference).

It is, in some embodiments, preferred to modify the internucleotide linkage from its normal phosphodiester to one that is more resistant to nuclease attack, such as phosphorothioate or boranophosphate—these two, being cleavable by RNase H, also allow that route of antisense inhibition in reducing the expression of the target gene.

Suitable sulphur (S) containing internucleotide linkages as provided herein may be preferred. Phosphorothioate internucleotide linkages are also preferred, particularly for the gap region (B) of gapmers. Phosphorothioate linkages may also be used for the flanking regions (A and C, and for linking A or C to D, and within region D, as appropriate).

Regions A, B and C, may however comprise internucleotide linkages other than phosphorothioate, such as phosphodiester linkages, particularly, for instance when the use of nucleotide analogues protects the internucleotide linkages within regions A and C from endo-nuclease degradation—such as when regions A and C comprise LNA nucleotides.

The internucleotide linkages in the oligomer may be phosphodiester, phosphorothioate or boranophosphate so as to allow RNase H cleavage of targeted RNA. Phosphorothioate is preferred, for improved nuclease resistance and other reasons, such as ease of manufacture.

In one aspect of the oligomer of the invention, the nucleotides and/or nucleotide analogues are linked to each other by means of phosphorothioate groups.

It is recognised that the inclusion of phosphodiester linkages, such as one or two linkages, into an otherwise phosphorothioate oligomer, particularly between or adjacent to nucleotide analogue units (typically in region A and or C) can modify the bioavailability and/or bio-distribution of an oligomer—see WO2008/053314, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleotide linkage groups are phosphorothioate.

When referring to specific gapmer oligonucleotide sequences, such as those provided herein it will be understood that, in various embodiments, when the linkages are phosphorothioate linkages, alternative linkages, such as those disclosed herein may be used, for example phosphate (phosphodiester) linkages may be used, particularly for linkages between nucleotide analogues, such as LNA, units. Likewise, when referring to specific gapmer oligonucleotide sequences, such as those provided herein, when the C residues are annotated as 5' methyl modified cytosine, in various embodiments, one or more of the Cs present in the oligomer may be unmodified C residues. in some embodiments in some embodiments Oligomeric Compounds The oligomers of the invention may, in a specially preferred embodiment, be selected from the group consisting of: SEQ ID NO's: 1, 2, 3, or 4. In an even more preferred embodiment, the oligomers of the invention is selected from SEQ ID NO's: 3 or 4.

Conjugates

In the context the term "conjugate" is intended to indicate a heterogenous molecule formed by the covalent attachment ("conjugation") of the oligomer as described herein to one or more non-nucleotide, or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethylene glycol.

Therefore, in various embodiments, the oligomer of the invention may comprise both a polynucleotide region which typically consists of a contiguous sequence of nucleotides, and a further non-nucleotide region. When referring to the oligomer of the invention consisting of a contiguous nucleotide sequence, the compound may comprise non-nucleotide components, such as a conjugate component.

In various embodiments of the invention the oligomeric compound is linked to ligands/conjugates, which may be used, e.g. to increase the cellular uptake of oligomeric compounds. WO2007/031091 provides suitable ligands and conjugates, which are hereby incorporated by reference.

The invention also provides for a conjugate comprising the compound according to the invention as herein described, and at least one non-nucleotide or non-polynucleotide moiety covalently attached to said compound. Therefore, in various embodiments where the compound of the invention consists of a specified nucleic acid or nucleotide sequence, as herein disclosed, the compound may also comprise at least one non-nucleotide or non-polynucleotide moiety (e.g. not comprising one or more nucleotides or nucleotide analogues) covalently attached to said compound.

Conjugation (to a conjugate moiety) may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

The oligomers of the invention may also be conjugated to active drug substances, for example, aspirin, ibuprofen, a sulfa drug, an antidiabetic, an antibacterial or an antibiotic.

In certain embodiments the conjugated moiety is a sterol, such as cholesterol.

In various embodiments, the conjugated moiety comprises or consists of a positively charged polymer, such as a positively charged peptides of, for example between 1-50, such as 2-20 such as 3-10 amino acid residues in length, and/or polyalkylene oxide such as polyethylglycol (PEG) or polypropylene glycol—see WO 2008/034123, hereby incorporated by reference. Suitably the positively charged polymer, such as a polyalkylene oxide may be attached to the oligomer of the invention via a linker such as the releasable linker described in WO 2008/034123.

By way of example, the following conjugate moieties may be used in the conjugates of the invention:

group. In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl. In some embodiments, the functional moiety is self-cleaving. In other embodiments, the functional moiety is biodegradable. See e.g., U.S. Pat. No. 7,087,229, which is incorporated by reference herein in its entirety.

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis. In some embodiments, the oligomers are functionalized with a hindered ester containing an aminoalkyl linker, wherein the alkyl portion has the formula $(CH_2)_w$, wherein w is an integer ranging from 1 to 10, pref-

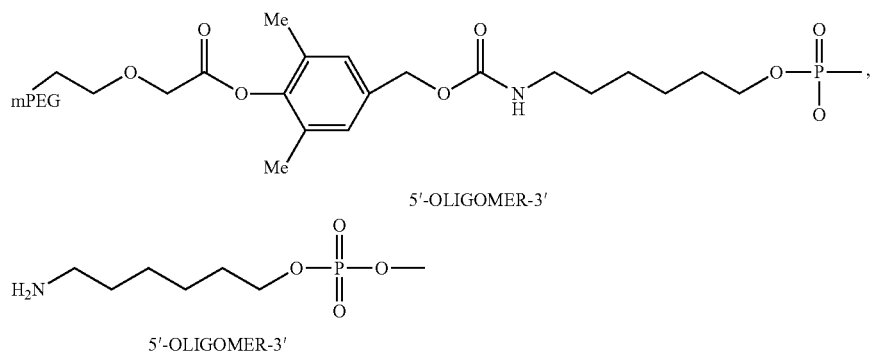

5'-OLIGOMER-3'

5'-OLIGOMER-3'

Activated Oligomers

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an $NH_2$ erably about 6, wherein the alkyl portion of the alkylamino group can be straight chain or branched chain, and wherein the functional group is attached to the oligomer via an ester group (—O—C(O)—$(CH_2)_w$NH).

In other embodiments, the oligomers are functionalized with a hindered ester containing a $(CH_2)_w$-sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group (—O—C(O)—$(CH_2)_w$SH)

In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular by methods disclosed in PCT Publication No. WO 2008/034122 and the examples therein, which is incorporated herein by reference in its entirety.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention may have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

Compositions

The oligomer of the invention may be used in pharmaceutical formulations and compositions. Suitably, such compositions comprise a pharmaceutically acceptable diluent, carrier, salt or adjuvant. PCT/DK2006/000512 provides suitable and preferred pharmaceutically acceptable diluent, carrier and adjuvants—which are hereby incorporated by reference. Suitable dosages, formulations, administration routes, compositions, dosage forms, combinations with other therapeutic agents, pro-drug formulations are also provided in PCT/DK2006/000512—which are also hereby incorporated by reference.

Applications

The oligomers of the invention may be utilized as research reagents for, for example, diagnostics, therapeutics and prophylaxis.

In research, such oligomers may be used to specifically inhibit the synthesis of PCSK9 protein (typically by degrading or inhibiting the mRNA and thereby prevent protein formation) in cells and experimental animals thereby facilitating functional analysis of the target or an appraisal of its usefulness as a target for therapeutic intervention.

In diagnostics the oligomers may be used to detect and quantitate PCSK9 expression in cell and tissues by northern blotting, in-situ hybridisation or similar techniques.

For therapeutics, an animal or a human, suspected of having a disease or disorder, which can be treated by modulating the expression of PCSK9 is treated by administering oligomeric compounds in accordance with this invention. Further provided are methods of treating a mammal, such as treating a human, suspected of having or being prone to a disease or condition, associated with expression of PCSK9 by administering a therapeutically or prophylactically effective amount of one or more of the oligomers or compositions of the invention. The oligomer, a conjugate or a pharmaceutical composition according to the invention is typically administered in an effective amount.

The invention also provides for the use of the compound or conjugate of the invention as described for the manufacture of a medicament for the treatment of a disorder as referred to herein, or for a method of the treatment of as a disorder as referred to herein.

The invention also provides for a method for treating a disorder as referred to herein said method comprising administering a compound according to the invention as herein described, and/or a conjugate according to the invention, and/or a pharmaceutical composition according to the invention to a patient in need thereof.

Medical Indications

The oligomers and other compositions according to the invention can be used for the treatment of conditions associated with over expression or expression of mutated version of the PCSK9.

The invention further provides use of a compound of the invention in the manufacture of a medicament for the treatment of a disease, disorder or condition as referred to herein.

Generally stated, one aspect of the invention is directed to a method of treating a mammal suffering from or susceptible to conditions associated with abnormal levels of PCSK9, comprising administering to the mammal and therapeutically effective amount of an oligomer targeted to PCSK9 that comprises one or more LNA units. The oligomer, a conjugate or a pharmaceutical composition according to the invention is typically administered in an effective amount.

The disease or disorder, as referred to herein, may, in some embodiments be associated with a mutation in the PCSK9 gene or a gene whose protein product is associated with or interacts with PCSK9. Therefore, in some embodiments, the target mRNA is a mutated form of the PCSK9 sequence.

An interesting aspect of the invention is directed to the use of an oligomer (compound) as defined herein or a conjugate as defined herein for the preparation of a medicament for the treatment of a disease, disorder or condition as referred to herein.

The methods of the invention are preferably employed for treatment or prophylaxis against diseases caused by abnormal levels of PCSK9.

Alternatively stated, In some embodiments, the invention is furthermore directed to a method for treating abnormal levels of PCSK9, said method comprising administering a oligomer of the invention, or a conjugate of the invention or a pharmaceutical composition of the invention to a patient in need thereof.

The invention also relates to an oligomer, a composition or a conjugate as defined herein for use as a medicament.

The invention further relates to use of a compound, composition, or a conjugate as defined herein for the manufacture of a medicament for the treatment of abnormal levels of PCSK9 or expression of mutant forms of PCSK9 (such as allelic variants, such as those associated with one of the diseases referred to herein).

Moreover, the invention relates to a method of treating a subject suffering from a disease or condition such as those referred to herein.

A patient who is in need of treatment is a patient suffering from or likely to suffer from the disease or disorder.

In some embodiments, the term 'treatment' as used herein refers to both treatment of an existing disease (e.g. a disease or disorder as herein referred to), or prevention of a disease, i.e. prophylaxis. It will therefore be recognised that treatment as referred to herein may, In some embodiments, be prophylactic.

In one embodiment, the invention relates to compounds or compositions comprising compounds for treatment of hypercholesterolemia and related disorders, or methods of treatment using such compounds or compositions for treating hypercholesterolemia and related disorders, wherein the term "related disorders" when referring to hypercholesterolemia refers to one or more of the conditions selected from the group consisting of: atherosclerosis, hyperlipidemia, HDL/LDL cholesterol imbalance, dyslipidemias, e.g., familial combined hyperlipidemia (FCHL), acquired hyperlipidemia, statin-resistant hypercholesterolemia, coronary artery disease (CAD), and coronary heart disease (CHD).

Embodiments

The following embodiments of the present invention may be used in combination with the other embodiments described herein.

1. An oligomer of between 10-30 nucleotides in length which comprises a contiguous nucleotide sequence of a total of between 10-30 nucleotides, wherein said contiguous nucleotide sequence is at least 80% homologous to a region corresponding to a mammalian PCSK9 gene or the reverse complement of an mRNA, such as SEQ ID NO: 5 or naturally occurring variant thereof.
2. The oligomer according to embodiment 1, wherein the contiguous nucleotide sequence is at least 80% homologous to a region corresponding to any of SEQ ID NO: 6-9.
3. The oligomer according to embodiments 1 or 2, wherein the contiguous nucleotide sequence comprises no mismatches or no more than one or two mismatches with the reverse complement of the corresponding region of SEQ ID NO: 5.
4. The oligomer according to any one of embodiments 1-3, wherein the nucleotide sequence of the oligomer consists of the contiguous nucleotide sequence.
5. The oligomer according to any one of embodiments 1-4, wherein the contiguous nucleotide sequence is between 10-18 nucleotides in length.
6. The oligomer according to any one of embodiments 1-5, wherein the contiguous nucleotide sequence comprises nucleotide analogues.
7. The oligomer according to embodiment 6, wherein the nucleotide analogues are sugar modified nucleotides, such as sugar modified nucleotides selected from the group consisting of: Locked Nucleic Acid (LNA) units; 2'-O-alkyl-RNA units, 2'-OMe-RNA units, 2'-amino-DNA units, and 2'-fluoro-DNA units.
8. The oligomer according to embodiment 6, wherein the nucleotide analogues are LNA.
9. The oligomer according to any one of embodiments 6-8 which is a gapmer.
10. The oligomer according to any one of embodiments 1-9, which inhibits the expression of PCSK9 gene or mRNA in a cell which is expressing PCSK9 gene or mRNA.
11. The oligomer according to any one of embodiments 1-10, wherein the oligomer consist of or comprises any one of SEQ ID NO's: 1, 2, 3, or 4,
12. A conjugate comprising the oligomer according to any one of embodiments 1-11, and at least one non-nucleotide or non-polynucleotide moiety covalently attached to said oligomer.
13. A pharmaceutical composition comprising the oligomer according to any one of embodiments 1-11, or the conjugate according to embodiment 12, and a pharmaceutically acceptable diluent, carrier, salt or adjuvant.
14. The oligomer according to any one of embodiments 1-11, or the conjugate according to embodiment 12, for use as a medicament, such as for the treatment of hypercholesterolemia and related disorders.
15. The use of an oligomer according to any one of the embodiments 1-11, or a conjugate as defined in embodiment 12, for the manufacture of a medicament for the treatment of hypercholesterolemia and related disorders.
16. A method of treating hypercholesterolemia and related disorders, said method comprising administering an effective amount of an oligomer according to any one of the embodiments 1-11, or a conjugate according to embodiment 12, or a pharmaceutical composition according to embodiment 13, to a patient suffering from, or likely to suffer from hypercholesterolemia and related disorders.
17. A method for the inhibition of PCSK9 in a cell which is expressing PCSK9, said method comprising administering an oligomer according to any one of the embodiments 1-11, or a conjugate according to embodiment 12 to said cell so as to inhibit PCSK9 in said cell.

EXAMPLES

LNA monomer and oligonucleotide synthesis were performed using the methodology referred to in Examples 1 and 2 of PCT/EP2007/060703.

The stability of LNA oligonucleotides in human or rat plasma is performed using the methodology referred to in Example 4 of PCT/EP2007/060703

The treatment of in vitro cells with LNA anti-PCSK9 antisense oligonucleotides is performed using the methodology referred to in Examples 5 and 6 of PCT/EP2007/060703

The analysis of Oligonucleotide Inhibition of PCSK9 expression by PCSK9 specific quantitative PCR in both an in vitro and in vivo model is performed using the methodology referred to in example 7 and 8 of PCT/EP2007/060703.

In vitro analysis of dose response in cell culture of LNA antisense inhibition of Human and murine PCSK9 expression is performed using the methodology referred to in examples 9 and 10 of PCT/EP2007/060703 respectively.

Testing of cholesterol levels in mouse serum, LDL-receptor protein level in mouse liver, lipoprotein class composition in serum, is performed using the methodology referred to in examples 11-13 of PCT/EP2007/060703 respectively.

In vivo experiments using oligomers of the invention targeting PCSK9 and subsequent analysis are performed using the methods disclosed in examples 14-17 of PCT/EP2007/060703.

The above mentioned examples of PCT/EP2007/060703 are hereby specifically incorporated by reference.

Example 1

Design of the Oligonucleotide

In a specific preferred design of the oligonucleotides of the invention, oligomers comprising 12 nucleotide sequences of Table 2 are designed as 2-8-2 (LNA-DNA-LNA) oligomers, oligomers comprising 13 nucleotide sequences of Table 2 are designed as 3-8-2, or 2-8-3 (LNA-DNA-LNA) oligomers and oligomers comprising 14 nucleotide sequences of Table 2 are designed as 3-8-3 (LNA-DNA-LNA) oligomers, wherein the LNAs are independently selected from oxy-LNA, thio-LNA, and amino-LNA, in either of the D-β and L-α configurations or combinations thereof.

ferred embodiment, 12 mers are 2-8-2 (LNA-DNA-LNA). In a preferred embodiment, internucleoside bonds are fully thiolated. In a further preferred embodiment, all LNA are oxy-LNA such as beta-D-oxy-LNA m indicate (optional) 5' methylation (in connection with cytosines)

Specific LNA oligomer compounds are shown in Table 3:

TABLE 3

| Compound ID # | Sequence | Corresponding SEQ ID # |
|---|---|---|
| 1 | 5'- $G_s G_s t_s a_s g_s t_s g_s g_s a_s g_s{}^m C_s G$ -3' | 1 |
| 2 | 5'- $A_s{}^m C_s g_s t_s g_s t_s t_s g_s t_s c_s T_s A_s{}^m C$ -3' | 2 |
| 3 | 5'- $G_s{}^m C_s A_s a_s c_s a_s g_s a_s g_s a_s g_s G_s A_s{}^m C$ -3' | 3 |
| 4 | 5'- $T_s G_s{}^m C_s t_s a_s c_s a_s a_s a_s a_s c_s{}^m C_s{}^m C_s A$ -3' | 4 |
| 10 | 5'- $G_s T_s c_s t_s g_s t_s g_s g_s a_s a_s G^m{}_s C_s G$-3' | 10 |

Example 2

Assays

Antisense modulation of PCSK9 expression can be assayed in a variety of ways known in the art. For example, PCSK9 mRNA levels can be quantified by, e.g. Northern blot analysis, competitive polymerase chain reaction (PCR), or real-time PCR. Real-time quantitative PCR is presently preferred. RNA analysis can be performed on total cellular RNA or mRNA. Methods of RNA isolation and RNA analysis such as Northern blot analysis are routine in the art and is taught in, for example, Current Protocols in Molecular Biology, John Wiley and Sons.

TABLE 2

| SEQMOTIF ID SEQUENCE | SEQ ID | GAPMER DESIGN | SEQ ID | LNA GAPMERS |
|---|---|---|---|---|
| 6 GGTAGTGGAGCG | 11 | 5'- GGtagtggag$^m$CG -3' | 16 | 5'- $G_s G_s t_s a_s g_s t_s g_s g_s a_s g_s{}^m C_s G$ -3' |
| 7 ACGTGTTGTCTAC | 12 | 5'- A$^m$Cgtgttgtc TA$^m$C -3' | 17 | 5'- $A_s{}^m C_s g_s t_s g_s t_s t_s g_s t_s c_s T_s A_s{}^m C$ -3' |
| 8 GCAACAGAGAGGAC | 13 | 5'- G$^m$CAacagagagGA$^m$C -3' | 18 | 5'- $G_s{}^m C_s A_s a_s c_s a_s g_s a_s g_s a_s g_s G_s A_s{}^m C$ -3' |
| 9 TGCTACAAAACCCA | 14 | 5'- TG$^m$Ctacaaaac$^m$C$^m$CA -3' | 19 | 5'- $T_s G_s{}^m C_s t_s a_s c_s a_s a_s a_s a_s c_s{}^m C_s{}^m C_s A$ -3' |
| 21 GTCTGTGGAAGCG | 15 | 5'- GTctgtggaaG$^m$CG-3' | 20 | 5'- $G_s T_s c_s t_s g_s t_s g_s g_s a_s a_s G^m{}_s C^s G$-3' |

Motif sequence represents the sequences of bases.

Gapmer design sequences—capital letters are nucleotide analogue nucleotides, such as those described herein, small letters (not subscript or superscript) are DNA nucleotides. Nucleotide analogue cytosines may optionally be 5-methyl cytosine, internucleoside linkages may be as disclosed herein, preferably phosphorothioate.

LNA gapmers—capital letters are LNA units, such as beta-D-oxy-LNA, small letters (not subscript or superscript) are DNA units. LNA cytosines may optionally be 5-methyl cytosine, internucleoside linkages may be as disclosed herein, preferably phosphorothioate.

14 mers are shown as 3-8-3 (LNA-DNA-LNA), 13 mers are shown as 2-8-3 (LNA-DNA-LNA), but in an equally pre- Real-time quantitative (PCR) can be conveniently accomplished using the commercially iQ Multi-Color Real Time PCR Detection System available from BioRAD. Real-time Quantitative PCR is a technique well known in the art and is taught in for example Heid et al. Real time quantitative PCR, Genome Research (1996), 6: 986-994.

Example 3

In Vitro Model: Cell Culture

The effect of antisense compounds on target nucleic acid expression can be tested in any of a variety of cell types provided that the target nucleic acid is present at measurable levels. Target can be expressed endogenously or by transient or stable transfection of a nucleic acid encoding said nucleic acid.

The expression level of target nucleic acid can be routinely determined using, for example, Northern blot analysis, Quantitative PCR, Ribonuclease protection assays. The following cell types are provided for illustrative purposes, but other cell types can be routinely used, provided that the target is expressed in the cell type chosen.

Cells were cultured in the appropriate medium as described below and maintained at 37° C. at 95-98% humidity and 5% $CO_2$. Cells were routinely passaged 2-3 times weekly.

15PC3: Mouse prostate cancer cell line 15PC3 was purchased from ATCC and cultured in DMEM (Sigma) with 10% FBS+Glutamax I+non-essential amino acids+gentamicin.

Hepa1-6: Mouse liver cell line Hepa1-6 was purchased from ATCC and cultured in DMEM (Sigma) with 10% FBS+Glutamax I+non-essential amino acids+gentamicin.

HepG2: Human liver cell line HepG2 was purchased from ATCC and cultured in Eagle MEM (Sigma) with 10% FBS+Glutamax I+non-essential amino acids+gentamicin.

HuH-7: Human liver cell line HepG2 was purchased from ATCC and cultured in Eagle MEM (Sigma) with 10% FBS+Glutamax I+non-essential amino acids+gentamicin.

Example 4

In Vitro Model: Treatment with Antisense Oligonucleotide

Cell culturing and transfections: Huh-7 and 15PC3 cells were seeded in 6-well plates at 37° C. (5% $CO_2$) in growth media supplemented with 10% FBS, Glutamax I and Gentamicin. When the cells were 60-70% confluent, they were transfected in duplicates with different concentrations of oligonucleotides (0.04-25 nM) using Lipofectamine 2000 (5 µg/mL). Transfections were carried out essentially as described by Dean et al. (1994, JBC 269:16416-16424). In short, cells were preincubated for 7 min. with Lipofectamine in OptiMEM followed by addition of oligonucleotide to a total volume of 1.5 mL transfection mix per well. After 4 hours, the transfection mix was removed; cells were washed and grown at 37° C. for approximately 20 hours (mRNA analysis and protein analysis) in the appropriate growth medium. Cells were then harvested for protein and RNA analysis.

In the Gymnosis experiments HepG2 cells were used in 6 well plates without transfection agent, the oligonucleotides were dissolved in the media.

Example 5

In Vitro Model: Extraction of RNA and cDNA Synthesis

Total RNA Isolation

Total RNA was isolated using RNeasy mini kit (Qiagen). Cells were washed with PBS, and Cell Lysis Buffer (RTL, Qiagen) supplemented with 1% mercaptoethanol was added directly to the wells. After a few minutes, the samples were processed according to manufacturer's instructions.

First Strand Synthesis

First strand synthesis was performed using either OmniScript Reverse Transcriptase kit or M-MLV Reverse transcriptase (essentially as described by manufacturer (Ambion)) according to the manufacturer's instructions (Qiagen). When using OmniScript Reverse Transcriptase 0.5 µg total RNA each sample, was adjusted to 12 µl and mixed with 0.2 µl poly (dT)$_{12-18}$ (0.5 µg/µl) (Life Technologies), 2 µl dNTP mix (5 mM each), 2 µl 10×RT buffer, 0.5 µl RNAguard™ RNase Inhibitor (33 units/mL, Amersham) and 1 µl OmniScript Reverse Transcriptase followed by incubation at 37° C. for 60 min. and heat inactivation at 93° C. for 5 min.

When first strand synthesis was performed using random decamers and M-MLV-Reverse Transcriptase (essentially as described by manufacturer (Ambion)) 0.25 µg total RNA of each sample was adjusted to 10.8 µl in $H_2O$. 2 µl decamers and 2 µl dNTP mix (2.5 mM each) was added. Samples were heated to 70° C. for 3 min. and cooled immediately in ice water and added 3.25 µl of a mix containing (2 µl 10×RT buffer; 1 µl M-MLV Reverse Transcriptase; 0.25 µl RNAase inhibitor). cDNA is synthesized at 42° C. for 60 min followed by heating inactivation step at 95° C. for 10 min and finally cooled to 4° C.

Example 6

Results of $IC_{50}$ of Different LNA Oligonucleotides in Transfection Experiments PCSK9 mRNA expression was determined by real-time quantitative PCR in 15PC3 and Huh-7 cells after Lipofectamine transfection with compounds SEQ ID NOs 1-4 and 10. In the transfection experiments data are normalized to GAPDH and normalized to the mock control (FIGS. 1A and B). The five compounds were active in both cell lines. SEQ ID NOs 2-4 however, had in both cell lines lower $IC_{50}$ than SEQ ID NO: 1. SEQ ID NO 3 and 4 were surprisingly better than SEQ ID NO: 10. $IC_{50}$ values are based on the experiments with transfection of 0.04 to 25 nM into the cells (FIG. 2/Table 4).

TABLE 4

| | $IC_{50}$ values | | | | |
|---|---|---|---|---|---|
| | SEQ ID NO: 1 | SEQ ID NO: 2 | SEQ ID NO: 3 | SEQ ID NO: 4 | SEQ ID NO: 10 |
| IC50 Huh-7 | 7.270 | 0.765 | 0.216 | 0.033 | 0.565 |
| IC50 15PC3 | 5.736 | 1.674 | 0.378 | 0.126 | 3.144 |

PCSK9 mRNA expression was determined by real-time quantitative PCR in HepG2 cells after treatment with compounds SEQ ID NOs 1-4 and 10 without transfection agent. In the Gymnosis experiments data are normalized to the untreated control (cells in media without addition of saline or oligonucleotide). The results from the Gymnosis study (FIG. 3) verified the $IC_{50}$ results, showing that all compounds actively down-regulate PCSK9 with SEQ ID NO: 1 being the least potent compound. SEQ ID NO: 3 and 4 were better than SEQ ID NO 10.

Example 7

Results of Screening Different LNA Oligonucleotides In Vivo

In this study C57BL/6J female mice on a standard chow diet were administered the LNA oligonucleotides intravenously twice weekly for 2 weeks (Days 0, 3, 7, 10 and 14=total of 5 administrations) at 10 mg/kg of SEQ ID NO 1-4.

The oligonucleotides are human specific and it was therefore not possible to measure any activity/potency effect in the mouse study.

ALT and AST levels were determined in the blood serum, free from red blood cells, obtained from the mice at the time of sacrifice (48 hours after last administration). The activity of alanine-aminotransferase (ALT) and aspartate-aminotransferase (AST) in mouse serum was determined using an enzymatic assay (ABX Pentra A11A01627 (ALT) or A11A01629 (AST), Horiba ABX Diagnostics, France) according to the manufacturer's instruction but adjusted to 96-well format. In short, serum samples were diluted 2.5 fold with $H_2O$ and assayed in duplicate. After addition of 50 µl diluted sample or standard (multical from ABX Pentra, A11A01652) to each well, 200 µl of 37° C. ALT reagent mix was added to each well. Kinetic measurements were performed at 340 nm and 37° C. for 5 min with an interval of 30 s. Data were correlated to the 2-fold diluted standard curve and results were presented as ALT or AST activity in U/L.

Administration of any of the 4 LNA oligonucleotides resulted in a minor elevation of ALT—and AST activity measured at sacrifice (day 16)—relative to the control group (administered saline). The ALT levels were 1.2 to 2 times increased (FIG. 4A), and the AST levels were 1.1 to 1.5 higher than in the control group (FIG. 4B). It is evident from these experiments that the four oligonucleotides selected have a particularly beneficial safety profile.

Example 7

In Vivo Model: Non-Human Primates, Macaca fascicularis, Treatment with Antisense Oligonucleotide, Assessing Pharmacology i.e. LDL-Cholesterol Reduction, Confirming Mechanism i.e. ApoB, PCSK9 mRNA and Protein Down-Regulation and the Association Between Compound Levels in Tissue and Pharmacological Effect The pharmacological effect of the PCSK9 LNA antisense compounds can be tested by treating non-human primates such as *Macaca fascicularis* (Cynomolgus monkey) with repeated or a single dosing and assessed by measuring serum levels of LDL-cholesterol (LDL-C).

LDL-cholesterol (LDL-C), Apolipoprotein B (AboB), PCSK9 mRNA and protein as well as total cholesterol (TC), HDL-cholesterol (HDL-C), triglycerides (TG), glucose, alanine aminotransferase (ALT), Asparagine aminotransferase (AST), urea, creatinine can be assessed as described below to evaluate pharmacological, mechanistic and toxicological effects. Plasma and tissue oligonucleotide content can also be assessed as described below.

Naïve male cynomolgus monkeys (non-human primates) were treated with subcutaneous injections of the unformulated (dissolved in saline solution) LNA antisense compounds SEQ ID NO: 4 (Table 3) and SEQ ID NO: 10 (Table 3) at a weekly repeated dose level of 5 mg/kg (Day 7, 14, 21, 28), with an initial loading dose of 20 mg/kg (Day 0). LDL-C as well as other biochemical parameters were followed by weekly or more frequent blood samplings. Animals were sacrificed Day 30 and livers and kidneys were collected to assess parameters such as liver PCSK9 mRNA level and liver oligonucleotide content.

Figure 6:
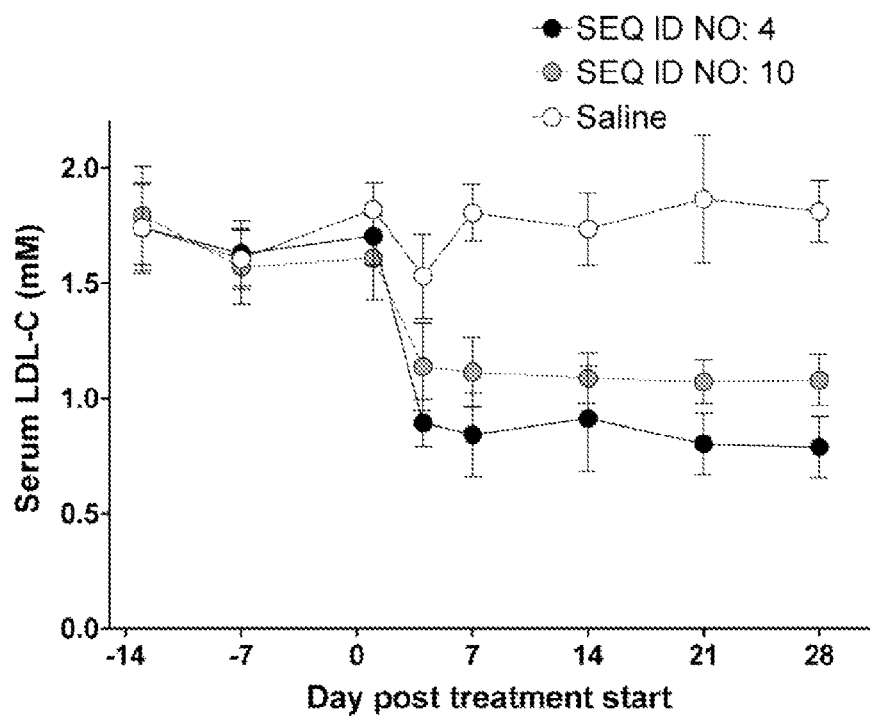
FIG. 6: Serum LDL-C over time in SEQ ID NO: 4 and 10 treated animals (mean and SEM, n=5)(species cynomolgus monkeys)
Figure 7:
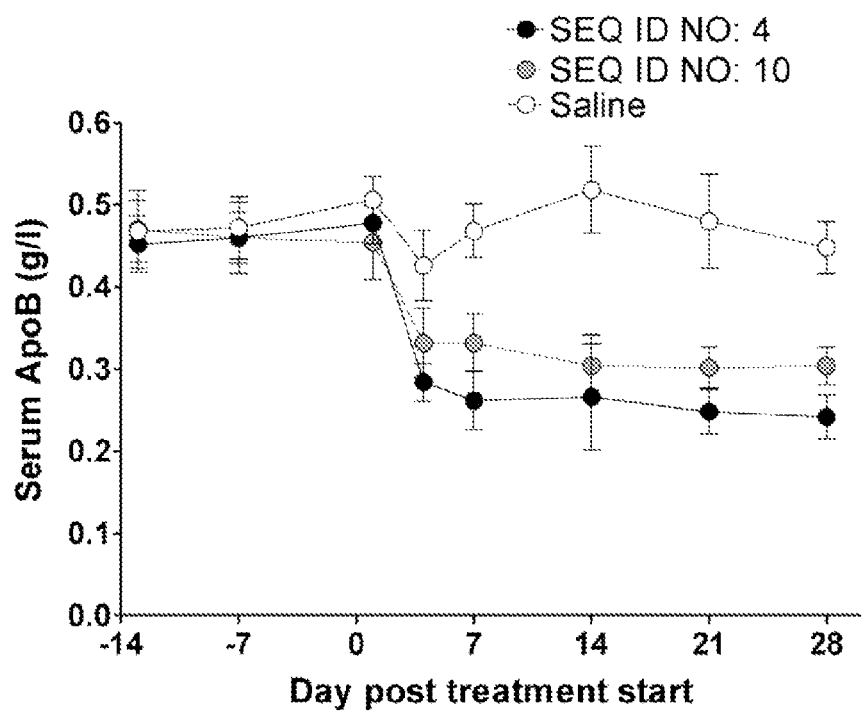
FIG. 7: Serum ApoB over time in SEQ ID NO: 4 and 10 treated animals (mean and SEM, n=5) (species cynomolgus monkeys)
Figure 8:
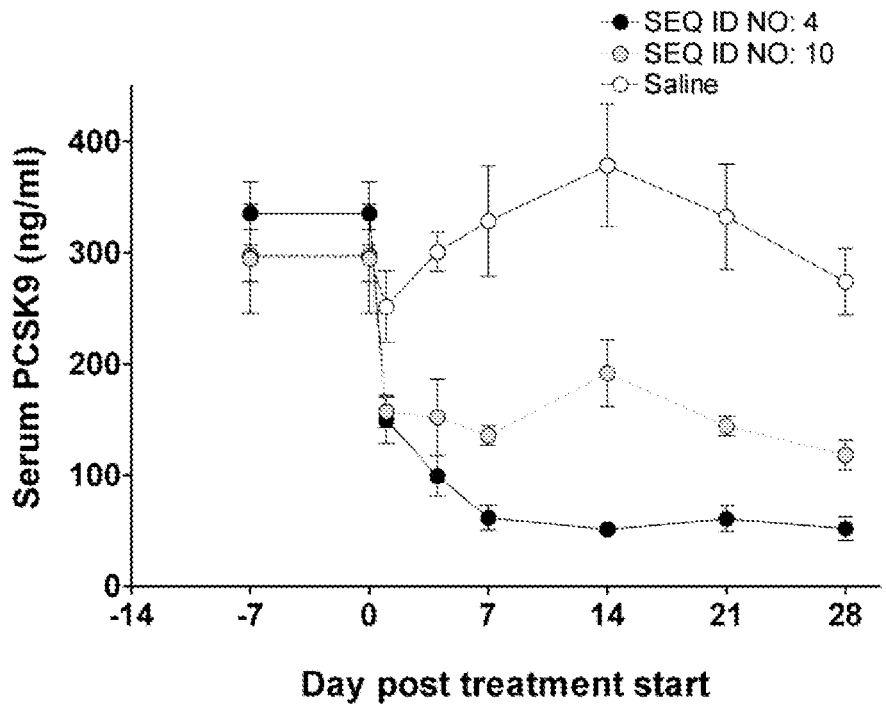
FIG. 8: Serum PSCK9 protein over time in SEQ ID NO: 4 and 10 treated animals (mean and SEM, n=5). Note: predose values Day-7 have been repeatedly plotted at Day 0 for illustrative purpose. (species cynomolgus monkeys)

Pharmacology, reduction of circulating LDL-C, was confirmed (significantly lower than saline control) without any unexpected side effects. SEQ ID NO: 4 reduced LDL-C to an average steady state level of approximately 50% below predose level (mean exceeded 50% reduction at several time points, with peak reductions in individual animals exceeding 70%) (FIG. 6). SEQ ID NO: 10 reduced LDL-C to an average steady state level of approximately 35% below pre-treatment level (with peak reduction in individual animals of 50%) (FIG. 6). The reductions in ApoB corresponded to the reductions in LDL-C (as they should, ApoB, essential protein component scaffolding the LDL-C particles) (FIG. 7). In both cases, SEQ ID NO: 4 had a surprisingly more potent effect over SEQ ID NO: 10. This was further established by looking at the target protein PCSK9 levels in serum, which were dramatically reduced by the SEQ ID NO: 4 treatment. PCSK9 serum protein levels had average reductions of 85% compared to predose (more reduction was observed in individual animals) (FIG. 8). SEQ ID NO: 10 also reduced plasma PCSK9 protein levels, however not to the same extent as SEQ ID NO: 4 (FIG. 8).

Figure 9:
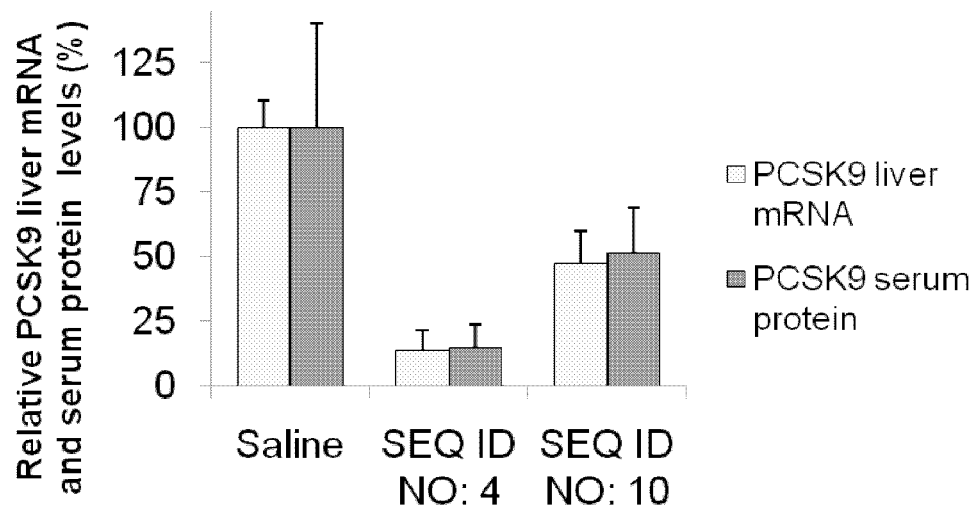
FIG. 9: PCKS9 liver mRNA and serum protein as percent of saline at sacrifice Day 30 of SEQ ID NO: 4 and 10 treated animals (means and SD, n=3). (species cynomolgus monkeys)

At sacrifice D30 (48 hours after last dose) PCSK9 liver mRNA levels were measured. These correlated well with the serum levels of PCSK9 protein and were significantly lower in SEQ ID NO: 4 treated animals (14% of the expression in saline treated animals) compared to SEQ ID NO: 10 treated (47% of saline level) (FIG. 9).

Figure 10:
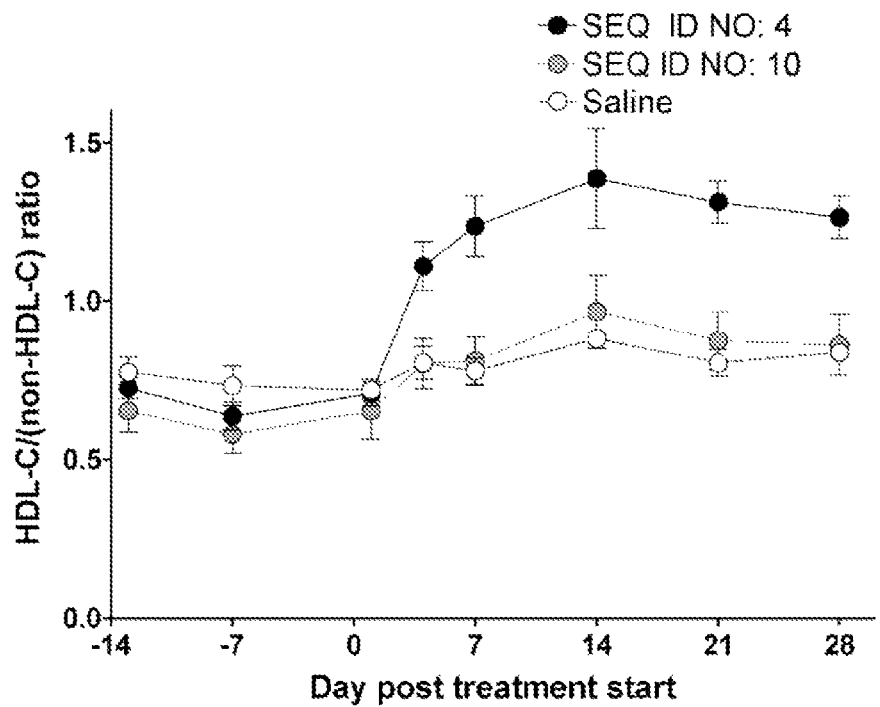
FIG. 10: HDL-C/(non-HDL-C) ratio over time in SEQ ID NO: 4 and 10 treated animals (mean and SEM, n=5). (species cynomolgus monkeys)

Clinical evidence points at HDL/non-HDL cholesterol ratio as being a better predictor than LDL cholesterol alone in terms of future risk for cardiovascular events in dyslipidemia patients. HDL-cholesterol (HDL-C) and total cholesterol (TC) were measured at different time points during the study in blood samples from the monkeys and the HDL/non-HDL cholesterol ratio calculated (HDL-C/(TC−HDL-C)). The ratio was improved by a 2-fold increase with SEQ ID NO: 4 and clearly display the specific therapeutic value and specificity of SEQ ID NO: 4 over SEQ ID NO: 10, which did not improve the ratio to the same extent (FIG. 10).

SEQ ID NO: 4 had a superior toxicological profile in the cynomolgus monkeys and induced no changes in any of the measured parameters in long term studies. SEQ ID NO: 4 showed no signs of changes in ALT, AST, creatinine or urea in the short term repeated dose study with sacrifice D30.

In addition a group of animals received only a single 10 mg/kg subcutaneous injection of SEQ ID NO: 4. One animal was sacrificed at each different time point after dosing (Day 4, 7, 14, 21, 28, 56). At termination serum LDL-C and liver oligonucleotide content were assessed.

Figure 11:
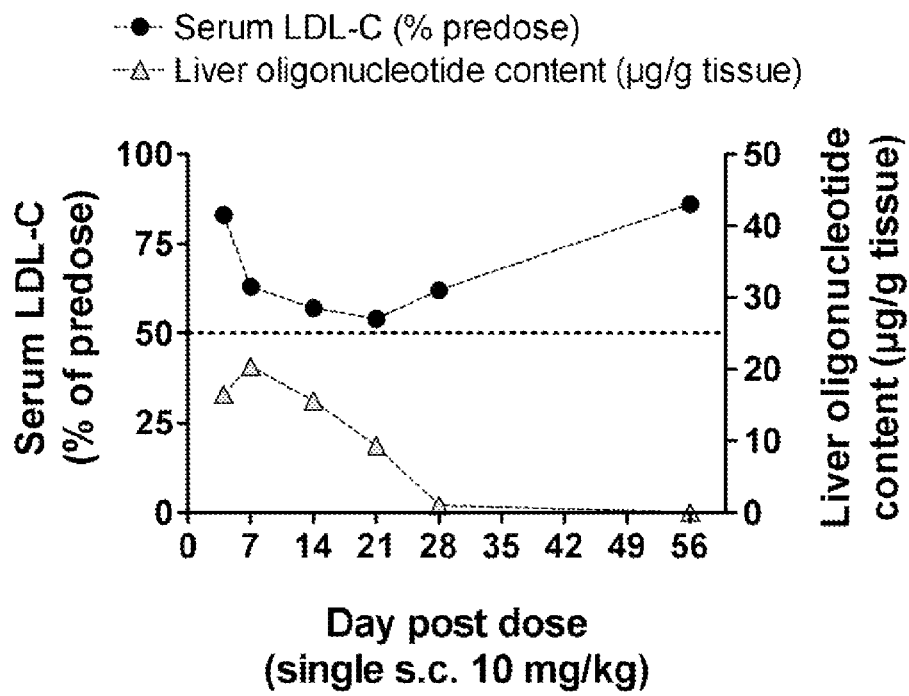
FIG. 11: Serum LDL-C and liver oligonucleotide content at different time points after a single 10 mg/kg s.c. dosing with SEQ ID NO: 4. Each time point is represented by one single animal in which both serum LDL-C and oligonucleotide content has been measured. (species cynomolgus monkeys)

After the single 10 mg/kg subcutaneous injection of SEQ ID NO: 4, LDL-C also approached a 50% reduction compared to predose and the reduction in LDL-C clearly correlated to the amount of drug (oligonucleotide) in the liver (FIG. 11).

Example Methods

Animals and Conditions

Cynomolgus monkeys (24-36 months old) had access to an expanded complete commercial primate diet (100 g/animal/ day special diet services: OWN (E) short SQC). The naïve male cynomolgus monkeys were treated with subcutaneous injections of the unformulated (dissolved in saline solution) LNA antisense compounds SEQ ID NO: 4 and SEQ ID NO: 10 at a weekly repeated dose level of 5 mg/kg (Day 7, 14, 21, 28), after an initial loading dose of 20 mg/kg (Day 0). LDL-C as well as other biochemical parameters were followed by weekly blood samplings. Animals were sacrificed Day 30 and livers and kidneys were collected to assess parameters as liver PCSK9 mRNA level and liver oligonucleotide content.

A group of animals only received a single 10 mg/kg subcutaneous injection of SEQ ID NO: 4. One animal was sacrifice at each different time point after dosing (Day 4, 7, 14, 21, 28, 56). At termination serum LDL-C and liver oligonucleotide content were assessed.

Blood samples were collected from the femoral veins before the first administration (Day −13 and −7) and weekly during the experiment prior to dosing, occasionally additional blood samples were collected. The animals were not provided food (i.e. fasted) over night before sampling.

Blood samples were analyzed for LDL-cholesterol (LDL-C), Apolipoprotein B (ApoB), serum PCSK9 protein (ELISA) as well as total cholesterol (TC), HDL-cholesterol (HDL-C), triglycerides (TG), glucose, alanine aminotransferase (ALT), aspartate aminotransferase (AST), urea and creatinine as described below to evaluate pharmacological and toxicological effects. Liver tissue was collected in RNAlater or snap frozen in liquid nitrogen to assess PCSK9 mRNA levels by qPCR, protein levels by western blot or oligonucleotide content as described below.

The cynomolgus primate study was conducted by a certified contract organization (AAALAC accredited and approved by the National Ministry of Agriculture) in accordance with the testing facility's standard operating procedure.

Serum Biochemical Analysis

All serum biochemical parameters were analyzed on an Olympus AU 640 fully automated analyzer.

The reagents sets used were the following:
Cholesterol total: package Olympus ref: OSR 6116
C.HDL: package Randox ref: CH 2652
C.LDL: package Randox ref: CH 2657
ApoB: package Randox ref: LP2117
Glucose, Olympus ref: OSR 6121
Urea, Olympus ref: OSR 6134
Triglycerides Olympus ref: OSR 61118
Creatinine Olympus ref: OSR 6178
Aspartate aminotransferase Olympus ref: OSR 6109
Alanine aminotransferase. Olympus ref: OSR 6107 qPCR, PCSK9 mRNA Analysis

Total RNA was extracted from liver tissue homogenates using RNeasy mini kit (Qiagen) spin columns according to the manufacturer's instructions. mRNA quantification of selected genes was carried out using commercially available TaqMan assays (Applied Biosystems, PCSK9, β-actin). First strand synthesis, cDNA was generated from total RNA by reverse transcription reaction using random decamers, 0.5 µg total RNA, and the M-MLV RT enzyme (Ambion) according to manufacturer's instructions. Applied Biosystems 7500 Fast Real-Time PCR instrument was used for amplification. Data were analyzed and quantified using the 7500 Fast SDS software. PCSK9 mRNA levels were normalized to β-actin and presented relative to saline controls as specified in the figures.

PCSK9 Protein ELISA

Serum PCSK9 protein content was analyzed with CircuLex™ human PCSK9 ELISA Kits in accordance with the manufacturer's instructions (MBL Int. Corp., MA, US). The assay was validated with serum from control animals (*Macaca fascicularis*) before commencing analyses.

Tissue and Plasma Oligonucleotide Analysis (Drug Content)

Sample and Standard Preparation

Tissue samples (100 mg) were collected in 2 ml Eppendorf tubes and kept on dry ice. Extraction buffer 500 µl (0.5% Igepal CA-630 (Sigma-Aldrich), 25 mM Tris pH 8.0, 25 mM EDTA, 100 mM NaCl, pH 8.0) containing proteinase K (1 mg/ml) (Sigma-Aldrich P4850) and two tungsten carbide beads (3 mm) were added. The samples were homogenized mechanically by a Retsch MM300 (8 min. at 25 revolutions per seconds) and homogenates were incubated overnight at 37° C. Control tissue from untreated animals were spiked with the relevant oligonucleotides at 5-250 µg/g tissue and treated as described for the samples above.

Extraction of Samples, Standard- and QC-Samples

One ml phenol-chloroform-isoamyl-alcohol (25:24:1(v/v/v)), saturated with 10 M Tris, pH 8.0, 1 mM EDTA (Sigma P2069) was added to each tissue samples and vortexed for 5 min. Phase separation was achieved by centrifugation at 4000 g for 15 min. The aqueous phase (upper-phase) was diluted 100 times. These dilutions were kept at 4° C. and were stable for up to two weeks.

Oligonucleotide Content Determination by ELISA.

Streptavidin-coated strips (Immobilizer Streptavidin LockWell module plate, Nunc) were washed three times in 300 µl 5×SSCT buffer (750 mM NaCl, 75 mM sodium citrate, 0.05% Tween-20, pH 7.0). Each well was incubated for 30 min. at room temperature under gentle agitation with 100 µl of a 0.02 µM solution of biotinylated capture probe (7-mer fully LNA-modified phosphodiester oligonucleotide complementary to the 5'-end oligonucleotide) in 5×SSCT buffer. The wells were aspirated and washed three times with 300 µl of 2×SSCT buffer (300 mM NaCl, 30 mM sodium citrate, 0.05% Tween-20, pH 7.0). One hundred microliters of the extracted and diluted oligonucleotide samples (pmol range) were added to the wells, which were agitated at room temperature for 0.5 hours. The wells were aspirated and washed three times with 300 µl of 2×SSCT buffer. One hundred microliters of a 0.025 µM solution of a 5'-digitoxinated conjugated (Dig) detection probe (5×SSCT buffer with 7-mer fully LNA modified phosphorodiester oligonucleotide, complementary to the 3'-end of the oligonucleotide) was added to each well and incubated for 1 hour at room temperature under gentle agitation. The wells were aspirated and washed three times with 300 µl of 2×SSCT buffer. One hundred microliters of anti-Dig-POD Fab fragments (Roche Applied Science) diluted 1:4000 in PBS containing 0.05% Tween-20 (pH 7.2) were added to each well and incubated for 1 hour at room temperature under gentle agitation. The wells were aspirated and washed three times with 300 µl of 2×SSCT buffer. One hundred microliters of substrate solution (TMB+Substrate-Chromogen, Dako) was added to each well and incubated for 3-5 min. at room temperature under gentle agitation, after which the incubation was stopped by addition of sulphuric acid (100 µl 0.5 M). The intensity of the color development was measured spectrophotometrically at 450 nm, and the test samples were referenced against the standard samples.

The invention claimed is:

1. A single stranded oligomer of between 10-18 nucleotides in length which comprises a contiguous nucleotide sequence selected from the group consisting of SEQ ID NO: 6, SEQ ID NO: 7, SEQ ID NO: 9, and SEQ ID NO: 21, or a contiguous nucleotide sequence with no more than one or two mismatches when compared to SEQ ID NO: 6, SEQ ID NO: 7, SEQ ID NO: 9, or SEQ ID NO: 21, wherein the oligomer is capable of recruiting RNase H when formed in a duplex with a complementary target RNA, and wherein the contiguous nucleotide sequence comprises one or more nucleotide analogues.

2. The oligomer according to claim 1, wherein the contiguous nucleotide sequence is selected from the group consisting of SEQ ID NO: 6, SEQ ID NO: 7, SEQ ID NO: 9, and SEQ ID NO: 21.

3. The oligomer according to claim 1, wherein the nucleotide sequence of the oligomer consists of the contiguous nucleotide sequence.

4. The oligomer according to claim 1, wherein the contiguous nucleotide sequence is between 12-16 nucleotides in length.

5. The oligomer according to claim 1, wherein the one or more nucleotide analogues are sugar modified nucleotides selected from the group consisting of: Locked Nucleic Acid (LNA) units, 2'-O-alkyl-RNA units, 2'-OMe-RNA units, 2'MOE units, 2'-amino-DNA units, and 2'-fluoro-DNA units.

6. The oligomer according to claim 5, wherein the one or more nucleotide analogues are LNA.

7. The oligomer according to claim 1 which is a gapmer selected from the group consisting of SEQ ID NO 11, SEQ ID NO: 12, SEQ ID NO: 14, and SEQ ID NO: 15.

8. The oligomer according to claim 7, wherein the oligomer is a LNA gapmer selected from the group consisting of SEQ ID NO: 16, SEQ ID NO: 17, SEQ ID NO: 19, and SEQ ID NO: 20.

9. The oligomer according to claim 1, which inhibits the expression of PCSK9 gene or mRNA in a cell which is expressing PCSK9 gene or mRNA.

10. The oligomer according to claim 8, wherein the oligomer consists of or comprises any one of SEQ ID NO: 1, SEQ ID NO: 2, SEQ ID NO: 4, and SEQ ID NO: 10.

11. A conjugate comprising the oligomer according to claim 1 and at least one non-nucleotide or non-polynucleotide moiety covalently attached to said oligomer.

12. A pharmaceutical composition comprising the oligomer according to claim 1, and a pharmaceutically acceptable diluent, carrier, salt or adjuvant.

13. The oligomer according to claim 1, which treats or prevents hypercholesterolemia and related disorders.

14. A method of treating hypercholesterolemia and related disorders, said method comprising administering an effective amount of the oligomer according to claim 1, to a patient suffering from, or likely to suffer from hypercholesterolemia and related disorders.

15. A method for the inhibition of PCSK9 in a cell which is expressing PCSK9, said method comprising administering the oligomer according to claim 1 to said cell so as to inhibit PCSK9 in said cell.

16. A pharmaceutical composition comprising the conjugate according to claim 11, and a pharmaceutically acceptable diluent, carrier, salt or adjuvant.

17. The oligomer according to claim 1, wherein said contiguous nucleotide sequence is connected by an internucleotide linkage selected from the group consisting of phosphodiester, phosphorothioate, and boranophosphate.

18. The oligomer according to claim 1, wherein said contiguous nucleotide sequence comprises at least one nucleobase selected from the group consisting of xanthine, hypoxanthine, 5-methylcytosine, isocytosine, pseudoisocytosine, 5-bromouracil, 5-propynuluracil, 6-aminopurine, 2-aminopurine, inosine, diaminopurine, and 2-chloro-6-aminopurine.

19. A method of increasing LDL receptor protein level in a cell comprising administering an effective amount of the oligomer according to claim 1 to said cell, wherein said oligomer inhibits PCSK9 mRNA level, thereby increasing LDL receptor protein expression.

20. A method of reducing cholesterol within a cell comprising administering an effective amount of the oligomer according to claim 1 to said cell, wherein said oligomer inhibits PCSK9 mRNA, thereby lowering cholesterol level.

21. The method of claim 14, wherein said disorder is selected from the group consisting of atherosclerosis, hyperlipidemia, HDL or LDL cholesterol imbalance, dyslipidemias, familial combined hyberlipidemia (FCHL), acquired hyperlipidemia, statin-resistant hypercholesterolemia, coronary artery disease (CAD), and coronary heart disease (CHD).

22. A method of detecting or quantitating PCSK9 mRNA level in a cell, comprising adding the oligomer of claim 1 and measuring the oligomer level bound to the PCSK9 mRNA in the cell.

* * * * *

SEQUENCE LISTING

<160> NUMBER OF SEQ ID NOS: 21

<210> SEQ ID NO 1
<211> LENGTH: 12
<212> TYPE: DNA
<213> ORGANISM: ARTIFICIAL
<220> FEATURE:
<223> OTHER INFORMATION: LNA Compound Oligomer sequence
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: beta-D-oxy LNA
<220> FEATURE:
<221> NAME/KEY: misc_feature
<222> LOCATION: (11)..(12)
<223> OTHER INFORMATION: beta-D-oxy LNA
<220> FEATURE:
<221> NAME/KEY: misc_feature
<222> LOCATION: (11)..(11)
<223> OTHER INFORMATION: 5-methyl cytosine

<400> SEQUENCE: 1
ggtagtggag cg                                                           12

<210> SEQ ID NO 2
<211> LENGTH: 13
<212> TYPE: DNA
<213> ORGANISM: ARTIFICIAL
<220> FEATURE:
<223> OTHER INFORMATION: LNA Compound Oligomer sequence
<220> FEATURE:
<221> NAME/KEY: misc_feature
<222> LOCATION: (1)..(13)
<223> OTHER INFORMATION: Phosphorothioate linkages
<220> FEATURE:
<221> NAME/KEY: misc_feature
<222> LOCATION: (1)..(2)
<223> OTHER INFORMATION: Beta-D-oxy-LNA
<220> FEATURE:
<221> NAME/KEY: misc_feature
<222> LOCATION: (2)..(2)
<223> OTHER INFORMATION: 5-methyl cytosine
<220> FEATURE:
<221> NAME/KEY: misc_feature
<222> LOCATION: (11)..(13)
<223> OTHER INFORMATION: Beta-D-oxy-LNA
<220> FEATURE:
<221> NAME/KEY: misc_feature
<222> LOCATION: (13)..(13)
<223> OTHER INFORMATION: 5-methyl cytosine

<400> SEQUENCE: 2
acgtgttgtc tac                                                          13

<210> SEQ ID NO 3
<211> LENGTH: 14
<212> TYPE: DNA
<213> ORGANISM: ARTIFICIAL
<220> FEATURE:
<223> OTHER INFORMATION: LNA Compound Oligomer sequence
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: beta-D-oxy LNA
<220> FEATURE:

```
<221> NAME/KEY: misc_feature
<222> LOCATION: (2)..(2)
<223> OTHER INFORMATION: 5-methyl cytosine
<220> FEATURE:
<221> NAME/KEY: misc_feature
<222> LOCATION: (12)..(14)
<223> OTHER INFORMATION: beta-D-oxy LNA
<220> FEATURE:
<221> NAME/KEY: misc_feature
<222> LOCATION: (14)..(14)
<223> OTHER INFORMATION: 5-methyl cytosine

<400> SEQUENCE: 3
gcaacagaga ggac                                                          14

<210> SEQ ID NO 4
<211> LENGTH: 14
<212> TYPE: DNA
<213> ORGANISM: ARTIFICIAL
<220> FEATURE:
<223> OTHER INFORMATION: LNA Compound Oligomer sequence
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: beta-D-oxy LNA
<220> FEATURE:
<221> NAME/KEY: misc_feature
<222> LOCATION: (3)..(3)
<223> OTHER INFORMATION: 5-methyl cytosine
<220> FEATURE:
<221> NAME/KEY: misc_feature
<222> LOCATION: (12)..(14)
<223> OTHER INFORMATION: beta-D-oxy LNA
<220> FEATURE:
<221> NAME/KEY: misc_feature
<222> LOCATION: (12)..(13)
<223> OTHER INFORMATION: 5-methyl cytosine

<400> SEQUENCE: 4
tgctacaaaa ccca                                                          14

<210> SEQ ID NO 5
<211> LENGTH: 3636
<212> TYPE: DNA
<213> ORGANISM: HOMO SAPIENS

<400> SEQUENCE: 5
cagcgacgtc gaggcgctca tggttgcagg cgggcgccgc cgttcagttc agggtctgag        60
cctggaggag tgagccaggc agtgagactg gctcgggcgg gccgggacgc gtcgttgcag       120
cagcggctcc cagctcccag ccaggattcc gcgcgcccct tcacgcgccc tgctcctgaa       180
cttcagctcc tgcacagtcc tccccaccgc aaggctcaag gcgccgccgg cgtggaccgc       240
gcacggcctc taggtctcct cgccaggaca gcaacctctc ccctggccct catgggcacc       300
gtcagctcca ggcggtcctg gtggccgctg ccactgctgc tgctgctgct gctgctcctg       360
ggtcccgcgg gcgcccgtgc gcaggaggac gaggacggcg actacgagga gctggtgcta       420
gccttgcgtt ccgaggagga cggcctggcc gaagcacccg agcacggaac cacagccacc       480
ttccaccgct gcgccaagga tccgtggagg ttgcctggca cctacgtggt ggtgctgaag       540
gaggagaccc acctctcgca gtcagagcgc actgcccgcc gctgcaggc ccaggctgcc       600 cgccggggat acctcaccaa gatcctgcat gtcttccatg gccttcttcc tggcttcctg       660
gtgaagatga gtggcgacct gctggagctg gccttgaagt tgcccatgt cgactacatc       720
```

-continued

```
gaggaggact cctctgtctt tgcccagagc atcccgtgga acctggagcg gattacccct    780
ccacggtacc gggcggatga ataccagccc cccgacggag gcagcctggt ggaggtgtat    840
ctcctagaca ccagcataca gagtgaccac cgggaaatcg agggcagggt catggtcacc    900
gacttcgaga atgtgcccga ggaggacggg acccgcttcc acagacaggc cagcaagtgt    960
gacagtcatg gcacccacct ggcaggggtg gtcagcggcc gggatgccgg cgtggccaag   1020
ggtgccagca tgcgcagcct cgcgtgctc aactgccaag gaagggcac ggttagcggc     1080
accctcatag gcctggagtt tattcggaaa agccagctgg tccagcctgt ggggccactg   1140
gtggtgctgc tgcccctggc gggtgggtac agccgcgtcc tcaacgccgc ctgccagcgc   1200
ctggcgaggg ctggggtcgt gctggtcacc gctgccggca acttccggga cgatgcctgc   1260
ctctactccc cagcctcagc tcccgaggtc atcacagttg gggccaccaa tgcccaagac   1320
cagccggtga ccctggggac tttggggacc aactttggcc gctgtgtgga cctctttgcc   1380
ccaggggagg acatcattgg tgcctccagc gactgcagca cctgctttgt gtcacagagt   1440
gggacatcac aggctgctgc ccacgtggct ggcattgcag ccatgatgct gtctgccgag   1500
ccggagctca ccctggccga gttgaggcag agactgatcc acttctctgc caaagatgtc   1560
atcaatgagg cctggttccc tgaggaccag cgggtactga cccccaacct ggtggccgcc   1620
ctgcccccca gcacccatgg ggcaggttgg cagctgtttt gcaggactgt atggtcagca   1680
cactcggggc ctacacggat ggccacagcc gtcgcccgct gcgccccaga tgaggagctg   1740
ctgagctgct ccagtttctc caggagtggg aagcggcggg gcgagcgcat ggaggcccaa   1800
gggggcaagc tggtctgccg ggcccacaac gcttttgggg gtgagggtgt ctacgccatt   1860
gccaggtgct gcctgctacc ccaggccaac tgcagcgtcc acacagctcc accagctgag   1920
gccagcatgg ggacccgtgt ccactgccac caacaggggc acgtcctcac aggctgcagc   1980
tcccactggg aggtggagga ccttggcacc cacaagccgc ctgtgctgag gccacgaggt   2040
cagcccaacc agtgcgtggg ccacagggag gccagcatcc acgcttcctg ctgccatgcc   2100
ccaggtctgg aatgcaaagt caaggagcat ggaatcccgg cccctcagga gcaggtgacc   2160
gtggcctgcg aggagggctg gacccctgact ggctgcagtg ccctccctgg gacctcccac   2220
gtcctggggg cctacgccgt agacaacacg tgtgtagtca ggagccggga cgtcagcact   2280
acaggcagca ccagcgaagg ggccgtgaca gccgttgcca tctgctgccg gagccggcac   2340
ctggcgcagg cctcccagga gctccagtga cagccccatc ccaggatggg tgtctgggga   2400
gggtcaaggc tggggctga gctttaaaat ggttccgact tgtccctctc tcagccctcc    2460
atggcctggc acgaggggat ggggatgctt ccgcctttcc ggggctgctg gcctggccct   2520
tgagtggggc agcctccttg cctggaactc actcactctg ggtgcctcct ccccaggtgg   2580
aggtgccagg aagctccctc cctcactgtg gggcatttca ccattcaaac aggtcgagct   2640
gtgctcgggt gctgccagct gctcccaatg tgccgatgtc cgtgggcaga atgactttta   2700
ttgagctctt gttccgtgcc aggcattcaa tcctcaggtc tccaccaagg aggcaggatt   2760
cttcccatgg ataggggagg gggcggtagg ggctgcaggg acaaacatcg ttgggggtg    2820
agtgtgaaag gtgctgatgg ccctcatctc cagctaactg tggagaagcc cctgggggct   2880
ccctgattaa tggaggctta gctttctgga tggcatctag ccagaggctg agacaggtg    2940
cgcccctggt ggtcacaggc tgtgccttgg tttcctgagc cacctttact ctgctctatg   3000
ccaggctgtg ctagcaacac ccaaaggtgg cctgcgggga gccatcacct aggactgact   3060
cggcagtgtg cagtggtgca tgcactgtct cagccaaccc gctccactac ccggcagggt   3120
```

-continued

```
acacattcgc acccctactt cacagaggaa gaaacctgga accagagggg gcgtgcctgc    3180
caagctcaca cagcaggaac tgagccagaa acgcagattg ggctggctct gaagccaagc    3240
ctcttcttac ttcacccggc tgggctcctc attttttacgg gtaacagtga ggctgggaag    3300
gggaacacag accaggaagc tcggtgagtg atggcagaac gatgcctgca ggcatggaac    3360
tttttccgtt atcacccagg cctgattcac tggcctggcg gagatgcttc taaggcatgg    3420
tcggggagga gggccaacaa ctgtccctcc ttgagcacca gccccaccca agcaagcaga    3480
catttatctt ttgggtctgt cctctctgtt gccttttttac agccaacttt tctagacctg    3540
ttttgctttt gtaacttgaa gatatttatt ctgggttttg tagcattttt attaatatgg    3600 tgactttttta aaataaaaac aaacaaacgt tgtcct                              3636
```

```
<210> SEQ ID NO 6
<211> LENGTH: 12
<212> TYPE: DNA
<213> ORGANISM: ARTIFICIAL
<220> FEATURE:
<223> OTHER INFORMATION: Oligomer sequence

<400> SEQUENCE: 6
ggtagtggag cg                                                          12

<210> SEQ ID NO 7
<211> LENGTH: 13
<212> TYPE: DNA
<213> ORGANISM: ARTIFICIAL
<220> FEATURE:
<223> OTHER INFORMATION: Oligomer sequence

<400> SEQUENCE: 7
acgtgttgtc tac                                                         13

<210> SEQ ID NO 8
<211> LENGTH: 14
<212> TYPE: DNA
<213> ORGANISM: ARTIFICIAL
<220> FEATURE:
<223> OTHER INFORMATION: Oligomer sequence

<400> SEQUENCE: 8
gcaacagaga ggac                                                        14

<210> SEQ ID NO 9
<211> LENGTH: 14
<212> TYPE: DNA
<213> ORGANISM: ARTIFICIAL
<220> FEATURE:
<223> OTHER INFORMATION: Oligomer sequence

<400> SEQUENCE: 9
tgctacaaaa ccca                                                        14

<210> SEQ ID NO 10
<211> LENGTH: 13
<212> TYPE: DNA
<213> ORGANISM: ARTIFICIAL
<220> FEATURE:
<223> OTHER INFORMATION: LNA Compound Oligomer sequence
<220> FEATURE:
<221> NAME/KEY: misc_feature
<222> LOCATION: (1)..(13)
<223> OTHER INFORMATION: Phosphorothioate linkages
<220> FEATURE:
<221> NAME/KEY: misc_feature
<222> LOCATION: (1)..(2)
```

```
<223> OTHER INFORMATION: beta-D-oxy LNA
<220> FEATURE:
<221> NAME/KEY: misc_feature
<222> LOCATION: (11)..(13)
<223> OTHER INFORMATION: beta-D-oxy LNA
<220> FEATURE:
<221> NAME/KEY: misc_feature
<222> LOCATION: (11)..(11)
<223> OTHER INFORMATION: 5-methyl cytosine

<400> SEQUENCE: 10
gtctgtggaa gcg                                                          13

<210> SEQ ID NO 11
<211> LENGTH: 12
<212> TYPE: DNA
<213> ORGANISM: ARTIFICIAL
<220> FEATURE:
<223> OTHER INFORMATION: Gapmer design Oligomer sequence
<220> FEATURE:
<221> NAME/KEY: misc_feature
<222> LOCATION: (1)..(12)
<223> OTHER INFORMATION: Optionally phosphorothioate linkages
<220> FEATURE:
<221> NAME/KEY: misc_feature
<222> LOCATION: (1)..(2)
<223> OTHER INFORMATION: nucleotide analogue
<220> FEATURE:
<221> NAME/KEY: misc_feature
<222> LOCATION: (11)..(12)
<223> OTHER INFORMATION: nucleotide analogue
<220> FEATURE:
<221> NAME/KEY: misc_feature
<222> LOCATION: (11)..(11)
<223> OTHER INFORMATION: Optionally 5-methyl cytosine

<400> SEQUENCE: 11
ggtagtggag cg                                                           12

<210> SEQ ID NO 12
<211> LENGTH: 13
<212> TYPE: DNA
<213> ORGANISM: ARTIFICIAL
<220> FEATURE:
<223> OTHER INFORMATION: Gapmer design Oligomer sequence
<220> FEATURE:
<221> NAME/KEY: misc_feature
<222> LOCATION: (1)..(13)
<223> OTHER INFORMATION: Optionally phosphorothioate linkages
<220> FEATURE:
<221> NAME/KEY: misc_feature
<222> LOCATION: (1)..(2)
<223> OTHER INFORMATION: nucleotide analogue
<220> FEATURE:
<221> NAME/KEY: misc_feature
<222> LOCATION: (2)..(2)
<223> OTHER INFORMATION: optionally 5-methyl cytosine
<220> FEATURE:
<221> NAME/KEY: misc_feature
<222> LOCATION: (11)..(13)
<223> OTHER INFORMATION: nucleotide analogue
<220> FEATURE:
<221> NAME/KEY: misc_feature
<222> LOCATION: (13)..(13)
<223> OTHER INFORMATION: optionally 5-methyl cytosine

<400> SEQUENCE: 12
acgtgttgtc tac                                                          13

<210> SEQ ID NO 13
<211> LENGTH: 14
<212> TYPE: DNA
<213> ORGANISM: ARTIFICIAL
<220> FEATURE:
```

```
<223> OTHER INFORMATION: Gapmer design Oligomer sequence
<220> FEATURE:
<221> NAME/KEY: misc_feature
<222> LOCATION: (1)..(14)
<223> OTHER INFORMATION: Optionally phosphorothioate linkages
<220> FEATURE:
<221> NAME/KEY: misc_feature
<222> LOCATION: (1)..(3)
<223> OTHER INFORMATION: nucleotide analogue
<220> FEATURE:
<221> NAME/KEY: misc_feature
<222> LOCATION: (2)..(2)
<223> OTHER INFORMATION: Optionally 5-methyl cytosine
<220> FEATURE:
<221> NAME/KEY: misc_feature
<222> LOCATION: (12)..(14)
<223> OTHER INFORMATION: nucleotide analogue
<220> FEATURE:
<221> NAME/KEY: misc_feature
<222> LOCATION: (14)..(14)
<223> OTHER INFORMATION: Optionally 5-methyl cytosine

<400> SEQUENCE: 13
gcaacagaga ggac                                                       14

<210> SEQ ID NO 14
<211> LENGTH: 14
<212> TYPE: DNA
<213> ORGANISM: ARTIFICIAL
<220> FEATURE:
<223> OTHER INFORMATION: Gapmer design Oligomer sequence
<220> FEATURE:
<221> NAME/KEY: misc_feature
<222> LOCATION: (1)..(14)
<223> OTHER INFORMATION: Optionally phosphorothioate linkages
<220> FEATURE:
<221> NAME/KEY: misc_feature
<222> LOCATION: (1)..(3)
<223> OTHER INFORMATION: nucleotide analogue
<220> FEATURE:
<221> NAME/KEY: misc_feature
<222> LOCATION: (3)..(3)
<223> OTHER INFORMATION: Optionally 5-methyl cytosine
<220> FEATURE:
<221> NAME/KEY: misc_feature
<222> LOCATION: (12)..(14)
<223> OTHER INFORMATION: nucleotide analogue
<220> FEATURE:
<221> NAME/KEY: misc_feature
<222> LOCATION: (12)..(13)
<223> OTHER INFORMATION: Optionally 5-methyl cytosine

<400> SEQUENCE: 14
tgctacaaaa ccca                                                       14

<210> SEQ ID NO 15
<211> LENGTH: 13
<212> TYPE: DNA
<213> ORGANISM: ARTIFICIAL
<220> FEATURE:
<223> OTHER INFORMATION: Gapmer design Oligomer sequence
<220> FEATURE:
<221> NAME/KEY: misc_feature
<222> LOCATION: (1)..(13)
<223> OTHER INFORMATION: Optionally phosphorothioate linkages
<220> FEATURE:
<221> NAME/KEY: misc_feature
<222> LOCATION: (1)..(2)
<223> OTHER INFORMATION: nucleotide analogue
<220> FEATURE:
<221> NAME/KEY: misc_feature
<222> LOCATION: (11)..(13)
<223> OTHER INFORMATION: nucleotide analogue
<220> FEATURE:
<221> NAME/KEY: misc_feature
<222> LOCATION: (12)..(12)
```

-continued

<223> OTHER INFORMATION: Optionally 5-methyl cytosine

<400> SEQUENCE: 15
gtctgtggaa gcg                                                        13

<210> SEQ ID NO 16
<211> LENGTH: 12
<212> TYPE: DNA
<213> ORGANISM: ARTIFICIAL
<220> FEATURE:
<223> OTHER INFORMATION: LNA Oligomer sequence
<220> FEATURE:
<221> NAME/KEY: misc_feature
<222> LOCATION: (1)..(12)
<223> OTHER INFORMATION: Optionally phosphorothioate linkages
<220> FEATURE:
<221> NAME/KEY: misc_feature
<222> LOCATION: (1)..(2)
<223> OTHER INFORMATION: LNA nucleotide analogue
<220> FEATURE:
<221> NAME/KEY: misc_feature
<222> LOCATION: (11)..(12)
<223> OTHER INFORMATION: LNA nucleotide analogue
<220> FEATURE:
<221> NAME/KEY: misc_feature
<222> LOCATION: (11)..(11)
<223> OTHER INFORMATION: optionally 5-methyl cytosine

<400> SEQUENCE: 16
ggtagtggag cg                                                         12

<210> SEQ ID NO 17
<211> LENGTH: 13
<212> TYPE: DNA
<213> ORGANISM: ARTIFICIAL
<220> FEATURE:
<223> OTHER INFORMATION: LNA Oligomer sequence
<220> FEATURE:
<221> NAME/KEY: misc_feature
<222> LOCATION: (1)..(13)
<223> OTHER INFORMATION: Optionally phosphorothioate linkages
<220> FEATURE:
<221> NAME/KEY: misc_feature
<222> LOCATION: (1)..(2)
<223> OTHER INFORMATION: LNA nucleotide analogue
<220> FEATURE:
<221> NAME/KEY: misc_feature
<222> LOCATION: (2)..(2)
<223> OTHER INFORMATION: optionally 5-methyl cytosine
<220> FEATURE:
<221> NAME/KEY: misc_feature
<222> LOCATION: (11)..(13)
<223> OTHER INFORMATION: LNA nucleotide analogue
<220> FEATURE:
<221> NAME/KEY: misc_feature
<222> LOCATION: (13)..(13)
<223> OTHER INFORMATION: optionally 5-methyl cytosine

<400> SEQUENCE: 17
acgtgttgtc tac                                                        13

<210> SEQ ID NO 18
<211> LENGTH: 14
<212> TYPE: DNA
<213> ORGANISM: ARTIFICIAL
<220> FEATURE:
<223> OTHER INFORMATION: LNA Oligomer sequence
<220> FEATURE:
<221> NAME/KEY: misc_feature
<222> LOCATION: (1)..(14)
<223> OTHER INFORMATION: Optionally phosphorothioate linkages
<220> FEATURE:
<221> NAME/KEY: misc_feature
<222> LOCATION: (1)..(3)

```
<223> OTHER INFORMATION: LNA nucleotide analogue
<220> FEATURE:
<221> NAME/KEY: misc_feature
<222> LOCATION: (2)..(2)
<223> OTHER INFORMATION: Optionally 5-methyl cytosine
<220> FEATURE:
<221> NAME/KEY: misc_feature
<222> LOCATION: (12)..(14)
<223> OTHER INFORMATION: LNA nucleotide analogue
<220> FEATURE:
<221> NAME/KEY: misc_feature
<222> LOCATION: (14)..(14)
<223> OTHER INFORMATION: Optionally 5-methyl cytosine

<400> SEQUENCE: 18
gcaacagaga ggac                                                       14

<210> SEQ ID NO 19
<211> LENGTH: 14
<212> TYPE: DNA
<213> ORGANISM: ARTIFICIAL
<220> FEATURE:
<223> OTHER INFORMATION: LNA Oligomer sequence
<220> FEATURE:
<221> NAME/KEY: misc_feature
<222> LOCATION: (1)..(14)
<223> OTHER INFORMATION: Optionally phosphorothioate linkages
<220> FEATURE:
<221> NAME/KEY: misc_feature
<222> LOCATION: (1)..(3)
<223> OTHER INFORMATION: LNA nucleotide analogue
<220> FEATURE:
<221> NAME/KEY: misc_feature
<222> LOCATION: (3)..(3)
<223> OTHER INFORMATION: Optionally 5-methyl cytosine
<220> FEATURE:
<221> NAME/KEY: misc_feature
<222> LOCATION: (12)..(14)
<223> OTHER INFORMATION: LNA nucleotide analogue
<220> FEATURE:
<221> NAME/KEY: misc_feature
<222> LOCATION: (12)..(13)
<223> OTHER INFORMATION: Optionally 5-methyl cytosine

<400> SEQUENCE: 19
tgctacaaaa ccca                                                       14

<210> SEQ ID NO 20
<211> LENGTH: 13
<212> TYPE: DNA
<213> ORGANISM: ARTIFICIAL
<220> FEATURE:
<223> OTHER INFORMATION: LNA Oligomer sequence
<220> FEATURE:
<221> NAME/KEY: misc_feature
<222> LOCATION: (1)..(13)
<223> OTHER INFORMATION: Optionally phosphorothioate linkages
<220> FEATURE:
<221> NAME/KEY: misc_feature
<222> LOCATION: (1)..(2)
<223> OTHER INFORMATION: LNA nucleotide analogue
<220> FEATURE:
<221> NAME/KEY: misc_feature
<222> LOCATION: (11)..(13)
<223> OTHER INFORMATION: LNA nucleotide analogue
<220> FEATURE:
<221> NAME/KEY: misc_feature
<222> LOCATION: (12)..(12)
<223> OTHER INFORMATION: Optionally 5-methyl cytosine

<400> SEQUENCE: 20
gtctgtggaa gcg                                                        13

<210> SEQ ID NO 21
```

```
<211> LENGTH: 13
<212> TYPE: DNA
<213> ORGANISM: ARTIFICIAL
<220> FEATURE:
<223> OTHER INFORMATION: Oligomer sequence

<400> SEQUENCE: 21
gtctgtggaa gcg                                                    13
```